United States Patent
Hossack et al.

(10) Patent No.: US 6,511,426 B1
(45) Date of Patent: Jan. 28, 2003

(54) MEDICAL DIAGNOSTIC ULTRASOUND SYSTEM AND METHOD FOR VERSATILE PROCESSING

(75) Inventors: John A. Hossack, Palo Alto, CA (US); Jeffrey S. Hastings, Los Altos, CA (US); Jeffrey M. Greenberg, Palo Alto, CA (US); Samuel H. Maslak, Woodside, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/328,113

(22) Filed: Jun. 8, 1999

Related U.S. Application Data

(63) Continuation of application No. 09/199,945, filed on Nov. 25, 1998, which is a continuation-in-part of application No. 09/089,060, filed on Jun. 2, 1998, which is a continuation-in-part of application No. 09/089,467, filed on Jun. 2, 1998, now abandoned.

(51) Int. Cl.$^7$ .................................. A61B 8/00
(52) U.S. Cl. ......................................... 600/437
(58) Field of Search ................. 600/443, 444, 600/445, 455, 447, 449, 448, 456, 437; 128/916

(56) References Cited

U.S. PATENT DOCUMENTS

| | | | |
|---|---|---|---|
| 6,210,328 B1 | * | 4/2000 | Robinson et al. ............ 600/437 |
| 6,059,727 A | * | 5/2000 | Fowlkes et al. .............. 128/916 |
| 6,155,978 A | * | 12/2000 | Cline et al. ................... 128/916 |

* cited by examiner

Primary Examiner—Francis J. Jaworski
Assistant Examiner—Maulin Patel

(57) ABSTRACT

A method and system for reducing speckle for two and three-dimensional images is disclosed. For two-dimensional imaging, a one and a half or a two-dimensional transducer is used to obtain sequential, parallel or related frames of elevation spaced data. The frames are compounded to derive a two-dimensional image. For three-dimensional imaging, various pluralities of two-dimensional frames of data spaced in elevation are compounded into one plurality of spaced two-dimensional frames of data. The frames of data are then used to derive a three dimensional set of data, such as by interpolation. Alternatively, the various pluralities are used to derive a three-dimensional set of data. An anisotropic filter is applied to the set of data. The anisotropic filter filters at least along the elevation dimension. In either situation, various displays may be generated from the final three-dimensional set of data. A method and system for adjustably generating two and three-dimensional representations is also disclosed. For three-dimensional imaging, at least two sets of three-dimensional data corresponding respectively to two types of Doppler or B-mode data are generated. The sets of data are then combined. An image or a quantity may be obtained from the combined data. By combining after generating the three-dimensional sets of data, the same data (sets of data) may be combined multiple times pursuant to different relationships. Thus, a user may optimize the image or quantity. Likewise, frames of data may be combined pursuant to different persistence parameters, such as different finite impulse response filter size and coefficients. The frames of data may then be re-combined pursuant to different persistence parameters. Original ultrasound data may also be used to re-generate an imaging using the same ultrasound image processes as used for a previous image.

90 Claims, 12 Drawing Sheets

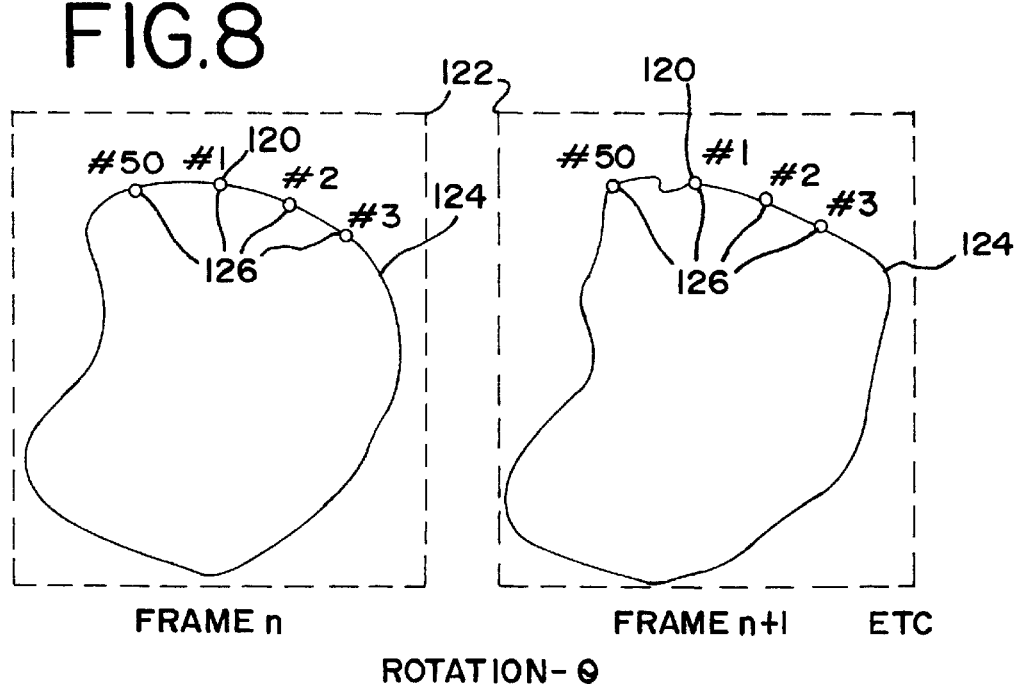
FIG.8
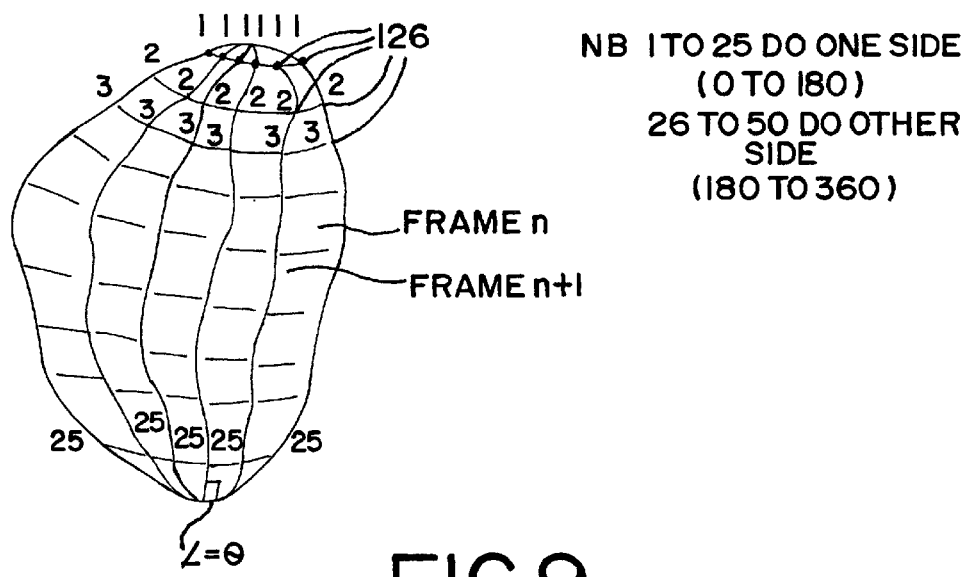
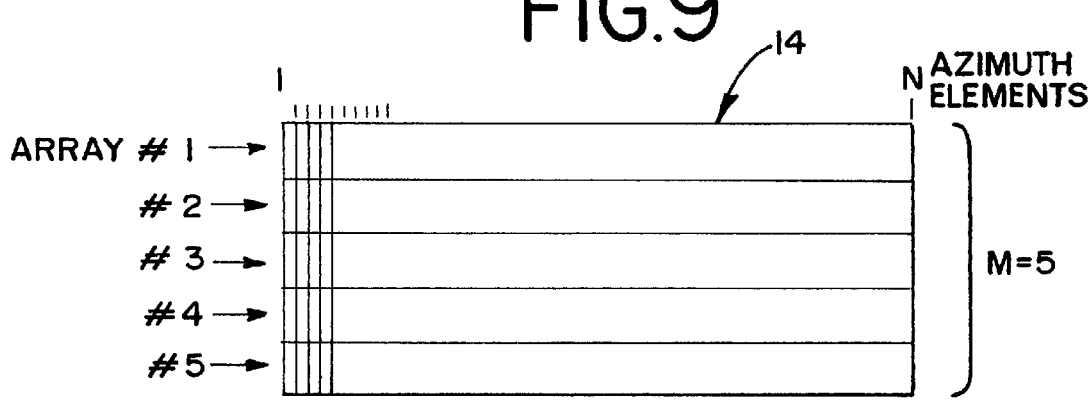
FIG.9

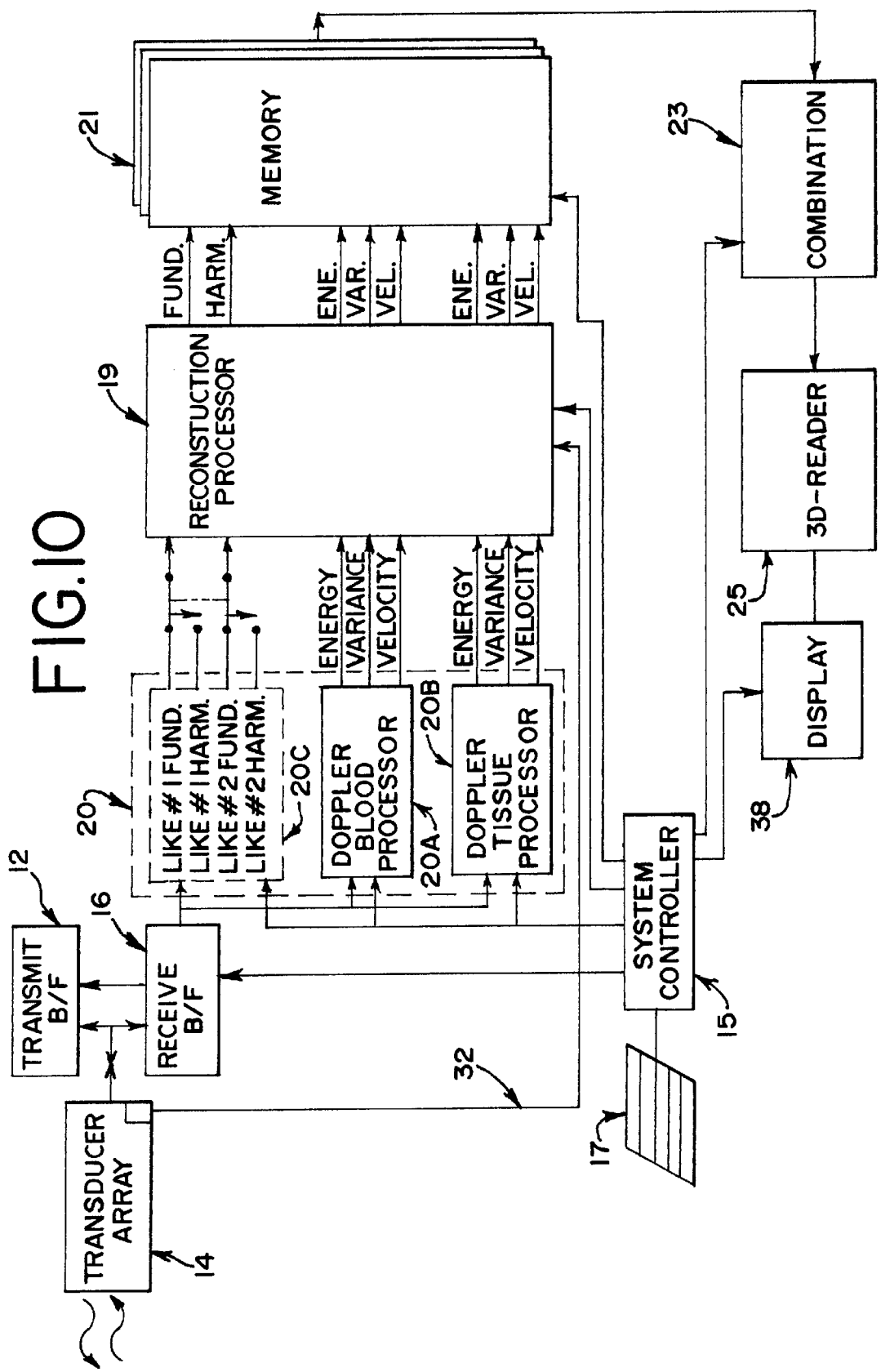

FIG.13A
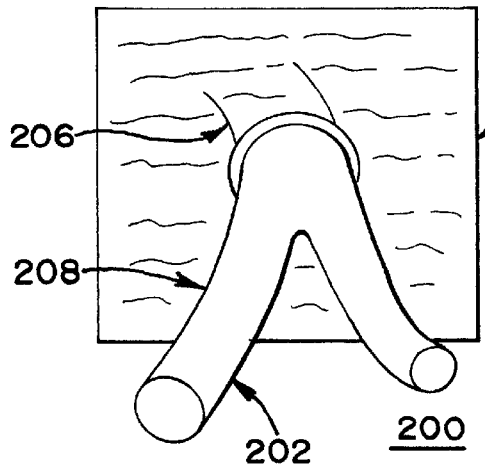
FIG.13B
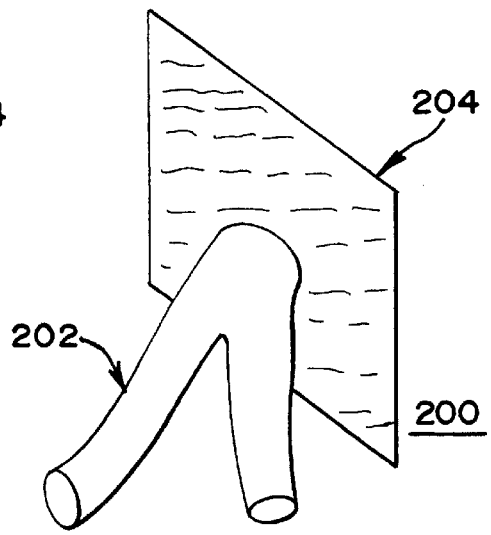
FIG.13C MULTIPLE ORIENTED B-MODE FRAMES - AT ARBITRARY ANGLES
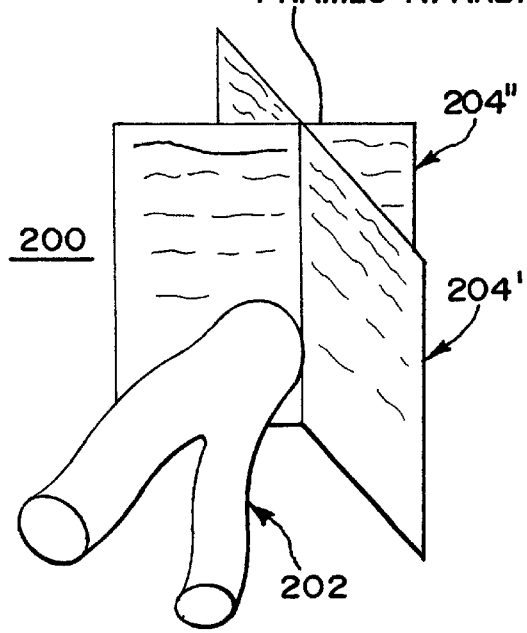
FIG.13D
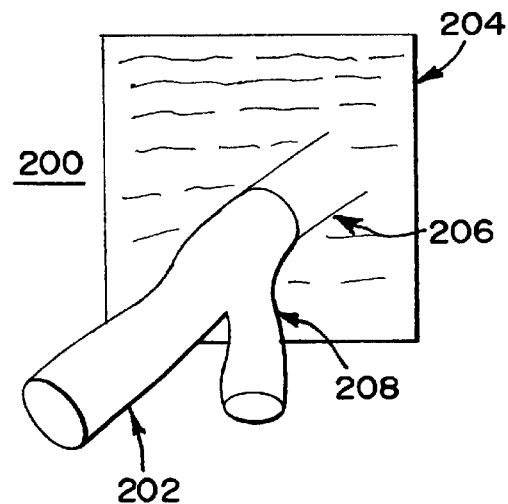

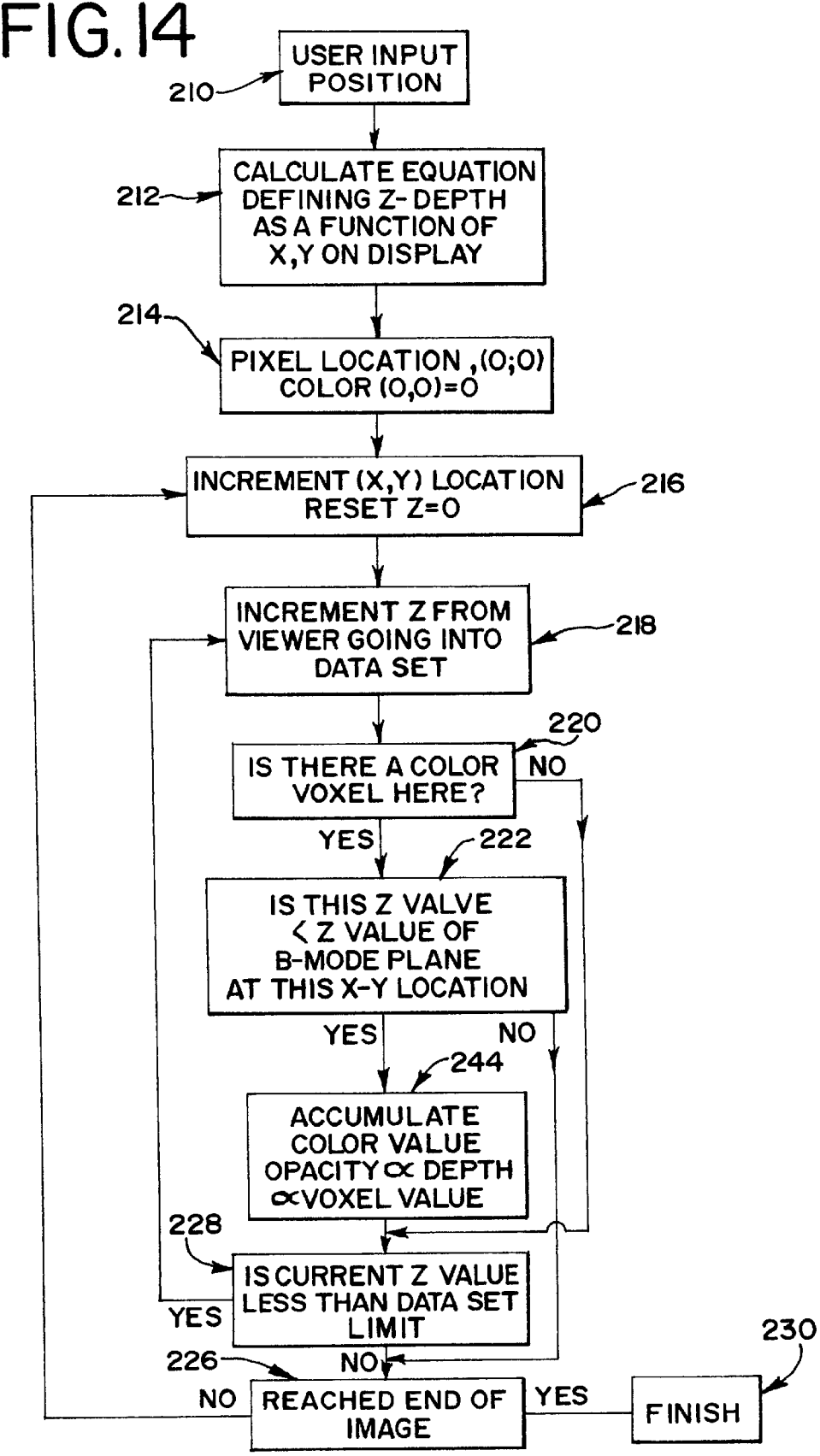

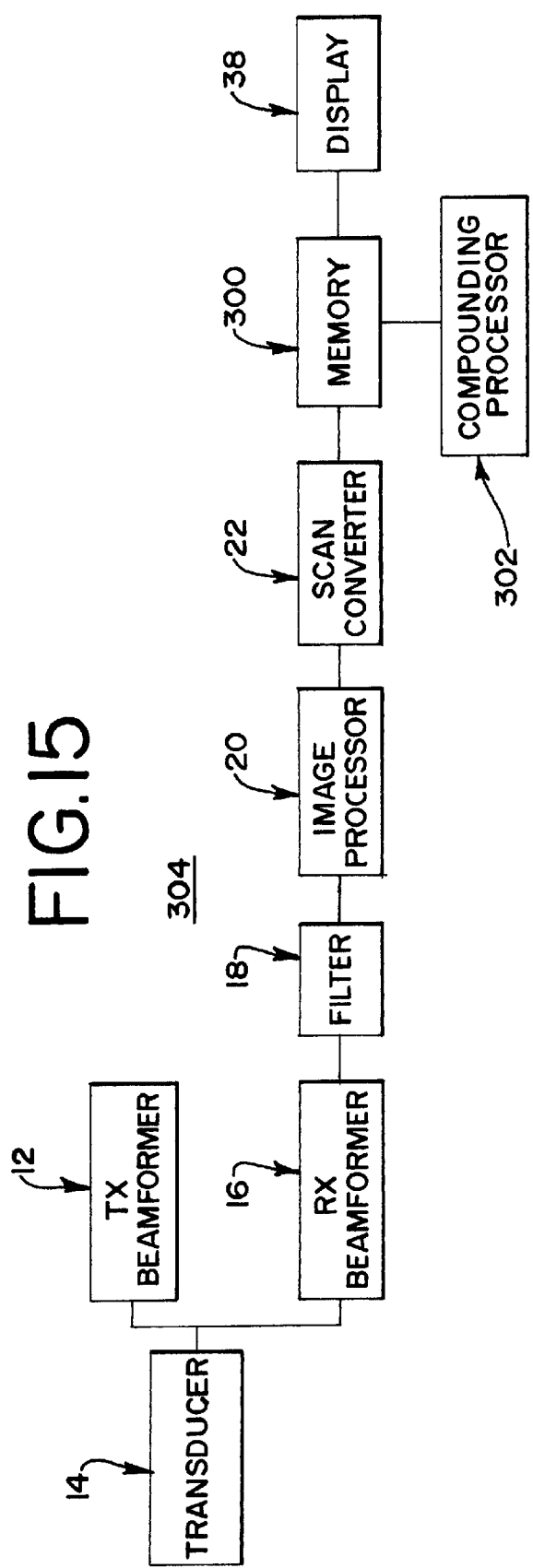

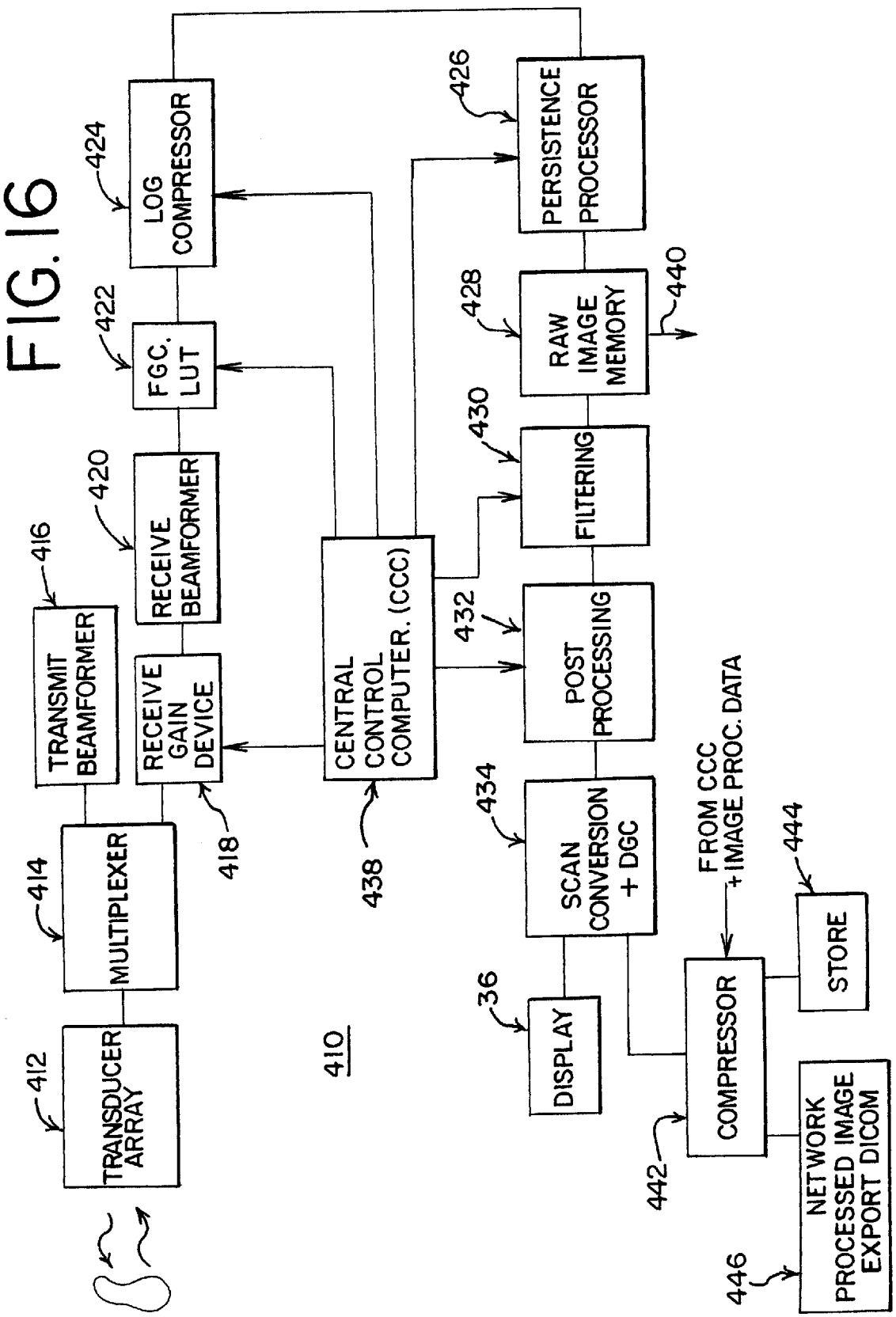

MEDICAL DIAGNOSTIC ULTRASOUND SYSTEM AND METHOD FOR VERSATILE PROCESSING

RELATED APPLICATIONS

This application is a continuation-in-part of U.S. patent application Ser. No. 09/199,945, filed Nov. 25, 1998, which is a continuation-in-part of Ser. Nos. 09/089,060 and 09/089,467 now abandoned, both filed on Jun. 2, 1998.

BACKGROUND

This invention relates to an ultrasound system and method for versatile processing, such as compounding ultrasound data. In particular, both three and two dimensional representations are generated with reduced speckle, Doppler and B-mode two and three-dimensional representations are generated in various changeable combinations, versatile persistence processing is provided, and versatile image re-generation is provided.

Ultrasound data for various modes of operation are typically used to generate one or more images. Modes of operation include B-mode, color Doppler, Doppler Tissue Imaging™ (see U.S. Pat. No. Re 35,720) and others. Conventional images include two and three-dimensional image representations.

As data is acquired, conventional systems mix different types of data to generate data for the image. For example, Doppler velocity data associated with Doppler energy data below a user or system set threshold is set to zero or assigned an appropriate color value. As another example, a plurality of frames of data are temporally persisted or filtered using an infinite impulse response filter. Typically, the mixing and other combination processing occurs as part of detection processing. The mixed data is then stored. The stored data is output and scan converted. The scan converted data is used to generate the image. However, to re-generate an image with different thresholds or other imaging parameters, data typically is re-acquired by scanning the patient.

There is growing interest in three-dimensional ultrasonic imaging, such as three dimensional ultrasound contrast agent imaging. To generate the three-dimensional image, volumetrically spaced information, such as planar or linear information, associated with positional information is obtained by using any of various transducers.

One approach is to use a two-dimensional transducer array to obtain three-dimensional image information directly. A two-dimensional array can be used to scan electronically in any desired orientation to acquire the desired information. Another approach is to collect multiple two-dimensional image data frames using a one-dimensional transducer array along with relative positional information among the image data frames so that these frames may be subsequently assembled in a three-dimensional volume to form the desired three-dimensional reconstruction.

Based on echo signals received from the transducer, the volumetric information, such as planar image information at a known orientation, is generated. The image information is derived as a function of various imaging modes. For example, B-mode or Color Doppler image information is generated. Once the volumetrically spaced information and associated positional information is provided, standard methods are employed for assembling the image information into a three-dimensional volume of the subject and for providing an appropriate display such as a cross section, a surface rendering, or the like.

For three-dimensional imaging, the scan converted data used to generate the image is output to a separate processor or computer. The computer arranges a plurality of sets of data representing two dimensions into a data set representing three-dimensions. A three-dimensional representation is then generated and displayed. Alternatively, a two-dimensional array is used to directly acquire a 3D data set. If the user desires to alter the image, such as by using a different threshold, new data is obtained by scanning the patient and arranged into a data set representing three-dimensions.

European Patent Application No. 0 797 106 A2 discloses an ultrasound system for three-dimensional imaging. B-mode and one type of Doppler data are stored and then mixed. The mixing is controlled by user entered opacities. However, the user control and mixing are limited.

For two-dimensional ultrasonic imaging, the two-dimensional or planar image information is used to generate a display. Typically, the planar information is obtained using a one-dimensional transducer array.

For both three and two dimensional imaging, speckle (a type of noise signal in coherent imaging) may reduce contrast resolution. U.S. Pat. No. 5,653,235 discloses a system for reducing speckle for two-dimensional imaging. A two-dimensional transducer array produces multiple beams at different orientations. See column 5, lines 5–46. The multiple beams are used to reduce speckle.

SUMMARY

The present invention is defined by the following claims, and nothing in this section should be taken as a limitation on those claims. By way of introduction, the preferred embodiment described below includes a method and system for versatile processing of ultrasound data.

In a first aspect of the invention, a method and system for reducing speckle for three-dimensional images is provided. Various pluralities of two-dimensional frames of data spaced in elevation are compounded into one plurality of spaced two-dimensional frames of data. The frames of data are then used to derive a three dimensional set of data, such as by interpolation. Alternatively, the various pluralities of two-dimensional frames of data are used to derive the three-dimensional set of data. An anisotropic filter is applied to the set of data. The anisotropic filter filters at least along the elevation dimension. In either situation, various displays may be generated from the final three-dimensional set of data.

In a second aspect, a method and system for generating three-dimensional representations is provided. At least two sets of three-dimensional data corresponding respectively to two types of Doppler data are generated. The sets of data are then combined. An image or a quantity may be obtained from the combined data. By combining after generating the three-dimensional sets of data, the same data (sets of data) may be combined a plurality of times pursuant to different relationships. Thus, a user may optimize the image or quantity.

In a third aspect, the two sets of three-dimensional data correspond to two types of B-mode, such as fundamental and harmonic frequency data. The combination is performed in response to user selection of the relationship between the sets of data.

In a fourth aspect, a three-dimensional representation is combined with a two-dimensional representation. The two images may be combined in user selected or system determined orientations. The combination may be altered or changed.

In a fifth aspect, two or three-dimensional sets of data are stored. A user may then select any one of various levels of persistence or filtering to combine the sets of data. The sets may represent the same or different regions of the patient. Since the sets of data are stored separately, the combination may be performed multiple times to identify diagnostic information.

In a other aspects, JPEG or other compressed data is combined, and an amount of combination in various embodiments is controlled as a function of a correlation between the sets of data.

In yet further aspects, ultrasound data is processed in response to one or more ultrasound image processes and corresponding parameters. The ultrasound data and the ultrasound image process parameters are stored or transmitted for re-generation of the same image in response to the ultrasound data and the previously used ultrasound image process parameters. The ultrasound system used to generate a first image, a remote ultrasound system or a remote workstation may be used to re-generate the same image.

Other embodiments are possible. Further aspects and advantages of the invention are discussed below in conjunction with the preferred embodiments.

BRIEF DESCRIPTION OF THE DRAWINGS

FIG. 8 is a schematic representation for generating a three dimensional polygon mesh.

FIG. 9 is a graphic representation of one embodiment of a 1.5D transducer.

FIG. 10 is a block diagram of one embodiment of an ultrasound system for acquiring data for two or three-dimensional imaging.

FIGS. 13A–D are representations of various two and three-dimensional images.

FIG. 14 is a schematic representation of one embodiment of a method for generating a combined two and three-dimensional image.

FIG. 15 is a block diagram of one embodiment of an ultrasound system for adjustable compounding.

FIG. 16 is a block diagram of one embodiment of an ultrasound system for re-generating an image.

DETAILED DESCRIPTION OF PREFERRED EMBODIMENTS

Figure 1:
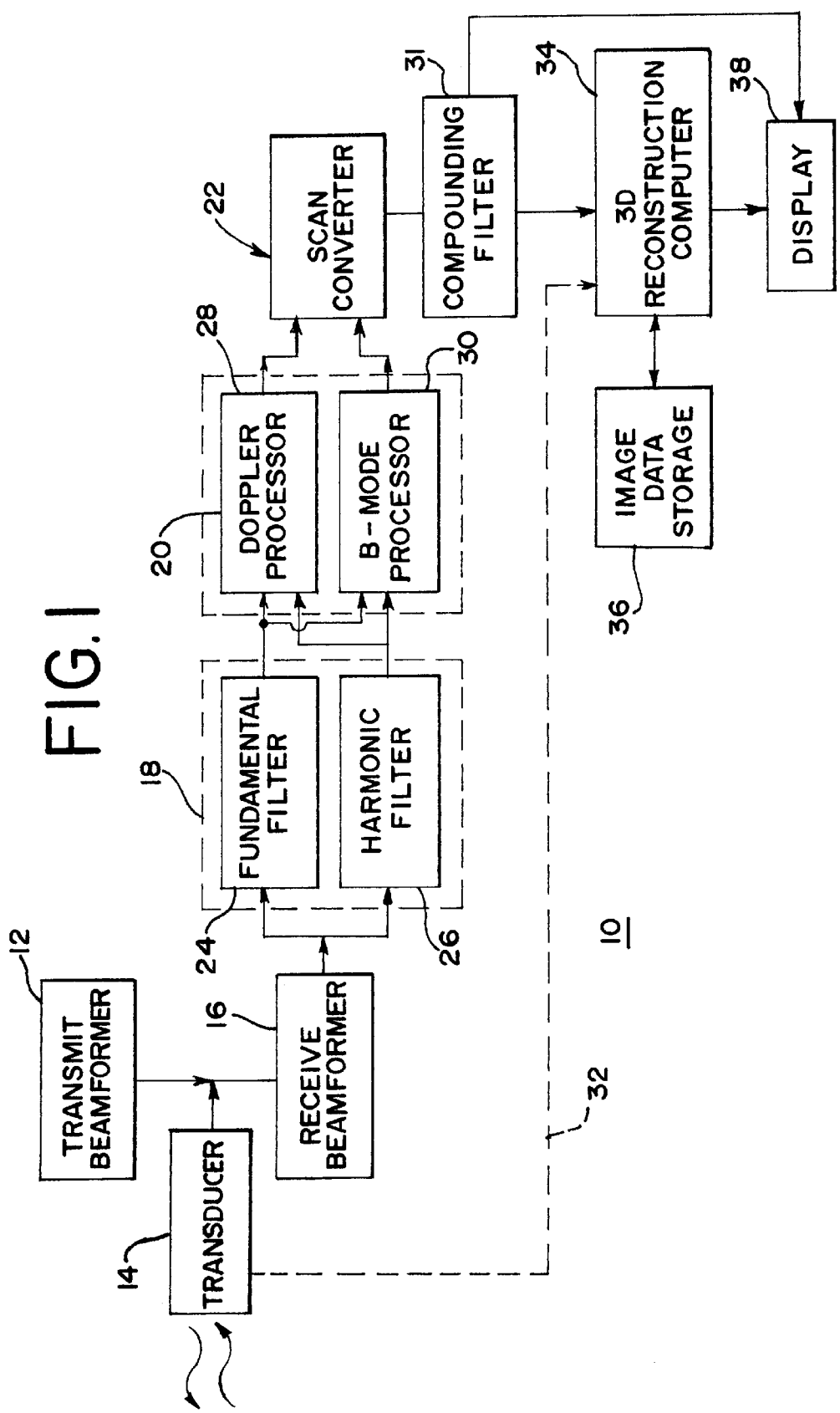
FIG. 1 is a block diagram of an ultrasound system for acquiring data for two or three-dimensional imaging.

The preferred embodiments described below are designed to provide for versatile combinations or re-generation of data and/or to reduce the effects of speckle in two and three-dimensional imaging by spatial compounding. Sets of data, whether representing two or three-dimensions, may be combined in various ways for various benefits. The following discussion addresses the various combinations or re-generation in four sections: Section 1—Speckle Reduction, Section 2—Enhanced Imaging, Section 3—Adjustable Persistence, and Section 4—Image Re-generation. Before addressing these sections, an overview of imaging considerations is provided.

Overview of Imaging Considerations

I. THREE-DIMENSIONAL IMAGING OVERVIEW

Four methods for acquiring data for three-dimensional imaging are described below, though other methods may be used. In the first method, a single element transducer (or an axially focused annular array) is mechanically scanned to sweep a volume or three-dimensional space. An example of this first method is the method practiced with the Medison-Kretz Combison 530 (Korea). Moving parts for sweeping the volume are enclosed in a fluid filled housing. Thus, the three-dimensional space is swept by mechanically moving (translating and/or rotating) the transducer over two-dimensions or at least two directions.

The second method is to use a two-dimensional transducer array to obtain three-dimensional image information directly. A two-dimensional array can be used to scan electronically in any desired orientation to acquire the desired information. Typically, the two-dimensional array is sub-sampled. It is generally impractical to provide a fully sampled 2D array (e.g., 64×64 is 4096 elements). An example of a two-dimensional array is disclosed in U.S. Pat. No. 5,329,496 (Smith). An imaging system for use with the disclosed array is described in U.S. Pat. No. 5,546,807 (Oxaal et al.). Another example of a two-dimensional array for use in the present invention is disclosed in U.S. Pat. No. 5,671,746 (Dreschel et al.).

The third method is to collect multiple two-dimensional image data frames associated with relative positional information using a one-dimensional transducer array. The two-dimensional image data frames or image planes are non-coplanar, such as two or more rotationally offset planes or two or more parallel planes offset in elevational position. The positional information provides the relative position among the image data frames so that these frames may be subsequently assembled in a three-dimensional volume to form the desired three-dimensional reconstruction. One dimension is electronically scanned and another dimension is mechanically scanned by rotation, translation, or any combination thereof For example, the transducer is swept. Sweeping corresponds to rotating the transducer about an axis along the azimuth of the lens surface.

One approach for this third method is to use manual motion detection techniques based on analysis of ultrasonic images. See Tamura et al., "Three-Dimensional Reconstruction of Echocardiograms Based on Orthogonal Sections" (Pattern Recognition, 18, 2, pp. 115–124, 1985).

Another approach is to sense position based on image motion detection, such as disclosed in MULTIPLE ULTRA-SOUND IMAGE REGISTRATION SYSTEM, METHOD AND TRANSDUCER, U.S. application Ser. No. 08/621,561 (filed Mar. 25, 1996), Ser. No. 08/807,498 (filed Feb. 27, 1997) and Ser. No. 08/916,585 (filed Aug. 22, 1997,) to Hossack et al., the disclosures of which are herein incorporated by reference. The position information is calculated from scan data.

U.S. Pat. No. 5,474,073 to Schwartz describes a qualitative three-dimensional approach using a hand-held transducer array and an assumed scan motion. The transducer is moved manually by free hand motion. The spacing between each two-dimensional image is assumed to be equal.

U.S. Pat. No. 5,353,354 to Keller discloses yet another approach. Accelerometers or magnetic sensors on a transducer measure the position and orientation of the transducer, and, therefore, relative motion between respective image planes. The free hand movement of the transducer is monitored. Suitable magnetic positioning sensors are described in U.S. Pat. Nos. 4,945,305 and 4,849,692 to Blood. Preferably, a pulsed DC type position sensor is used for this type of transducer. Such systems include the mini Bird™ and Flock of Birds™ systems by Ascension Technology Corp. of Burlington, Vt. Alternatively, the 3Space Fastrak from Polhemus (Colchester, Vt.) is used.

Mechanical manipulation guides or fixtures capable of rotation, translation, or a fan-like sweep may also be used to spatially orient each two-dimensional image plane. Such devices are disclosed in U.S. Pat. No. 5,454,371 (Fenster) and U.S. Pat. No. 5,562,095 (Downey et al.).

Another approach is to provide a spaced arrangement of LEDs, such as infra-red LEDs, on the transducer. The LEDs are activated in sequence and monitored by preferably two or more cameras. The position and orientation is then inferred from an image of the LEDs generated by the cameras. One such device is manufactured by Image Guided Technologies Inc., Boulder, Colo.

Still another approach is to use a spaced arrangement of microphones. See King U.S. Pat. No. 4,100,916. The position information is determined from the time of flight of acoustic impulses generated by a source on the transducer to the various microphones.

Yet another approach for acquiring multiple two-dimensional frames of data and positional information is to use a motorized array to collect the desired set of image data frames by precisely controlling the movement of the transducer array. One example is the Acuson V5M Transesophageal transducer, a rotating transducer. The rotating transducer produces two-dimensional images at known angles of rotation. A lens design for such a transducer is shown in U.S. Pat. No. 5,562,096 (Hossack, et al.). Another example is a transthoracic transducer, such as disclosed in U.S. Pat. No. 5,159,931 to Pini. See also, Sapoznikov et al., "Left Ventricular Shape, Wall Thickness and Function Based on Three-Dimensional Reconstruction Echocardiography", Computers in Cardiology, IEEE Computer Society Press, Cat CH 2476-0, pp. 495–498, 1987. A related approach is to use a large rotating transducer as described in McCann et al., "Multidimensional Ultrasonic Imaging for Cardiology", Proceedings of IEEE, 76, 9, pp. 1063–1072, September 1988. For example and preferably for use with harmonic imaging, an Acuson 3V2c and 4V2c transducer is placed in a rotatable fixture, such as disclosed in Pini or McCann.

The fourth method for acquiring data for three-dimensional imaging uses a single element transducer rotatable in one-dimension, a linear array unfocused or defocused in the elevational direction (such as by a concave lens with a len velocity less than that of tissue) or a two-dimensional array to scan a volume. As disclosed in U.S. Pat. No. 5,305,756 to Entrekin et al., a fan shaped beam focused in the azimuthal direction and divergent in the elevational direction is used to scan orthogonal to the longitudinal face of the transducer or in a sector axial to the transducer. By using known two-dimensional processing, each range sample corresponds to a summation or integration of various elevational positions corresponding to that range at a plurality of elevational positions in the fan shaped beam. A plurality of range samples corresponding to each line in the axial scan pattern is obtained. A two dimensional image is generated from the range samples (corresponding to integrated samples). The two dimensional image is a reconstruction of data representing a volume or three dimensions. Preferably, the first, second or third methods are used.

II. OTHER IMAGING CONSIDERATIONS:

Different methods with various transducers may also be used for two-dimensional imaging. For two-dimensional imaging, any of the various transducers discussed above may be used to mechanically or electrically scan a two-dimensional plane. Elevation positional information may not be needed since only one planar region is scanned. A plurality of frames of data representing the same region and corresponding to a respective plurality of types of data are acquired. Alternatively, the plurality of frames of data represent different elevation positions, such as caused by purposeful translation of the transducer or caused by unintentional movement of the transducer relative to the patient.

Two or three-dimensional images are based on receiving signals at various frequencies, such as a fundamental frequency or a harmonic frequency band or an intermediate frequency band associated with a fundamental transmit frequency band. Harmonic frequencies are frequencies associated with non-linear propagation or scattering of transmit signals. As used herein, harmonic includes subharmonics and fractional harmonics as well as second, third, fourth, and other higher harmonics. The harmonic frequency band may overlap the fundamental frequency band.

In tissue imaging, whether harmonic or fundamental, no additional non-linear contrast agent is added to the target, and only the characteristics of the tissue are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible. In this case, no contrast agent is introduced into the tissue at any time during the imaging session.

Tissue harmonic images may provide a particularly high spatial resolution and may possess improved contrast resolution characteristics. In particular, there may often be less clutter in the near field. Additionally, because the transmit beam is generated using the fundamental frequency, the transmit beam profile may be less distorted by a specific level of tissue-related phase aberration than would a transmit beam formed using signals transmitted directly at the second harmonic.

Imaging may be aided by the introduction of contrast agents. In contrast agent harmonic imaging, any one of a number of well known nonlinear ultrasound contrast agents, such as micro-spheres or the FS069 agent by Schering of Germany, is added to the target or subject in order to enhance the non-linear response of the tissue or fluid. The contrast agents radiate ultrasonic energy at the fundamental or harmonics of an insonifying energy at fundamental frequencies. However, contrast agents may not be necessary for three-dimensional imaging.

Section 1—Speckle Reduction

Compounding, such as spatial compounding prior to generation of the data set or as part of anisotropic filtering, may reduce the amount of speckle. Reducing speckle improves contrast resolution and aesthetics, particularly in three-dimensional imaging where the speckle may adversely affect two-dimensional representations generated from three-dimensional speckle.

I. THE ULTRASOUND SYSTEM

Referring now to the figures, and in particular, FIG. 1, an ultrasound system for two and three-dimensional imaging as discussed above is generally shown at 10. The ultrasound system 10 includes a transmit beamformer 12, a transducer array 14, a receive beamformer 16, a filter block 18, a signal processor block 20, and a scan converter 22. The ultrasound system 10 is configurable to acquire information corresponding to a plurality of two-dimensional representations or image planes of a subject for three-dimensional reconstruction or two-dimensional imaging. Other methods, such as those associated with a two dimensional or single element transducer array, may be used. To generate a plurality of two-dimensional representations of the subject during an imaging session, the ultrasound system 10 is configured to transmit, receive and process during a plurality of transmit events. Each transmit event corresponds to firing along an ultrasound scan line in the subject.

The transmit beamformer 12 is of a construction known in the art, such as a digital or analog based beamformer capable of generating signals at different frequencies. The transmit beamformer 12 generates one or more excitation signals. Each excitation signal has an associated center frequency. Preferably, the center frequency of the excitation signals is within the 1 to 15 MHz range, such as 2 MHz, and is selected to be suitable for the frequency response of the transducer array 14. The excitation signals preferably have non-zero bandwidth and are shaped to reduce energy in harmonic frequency bands as disclosed in U.S. Pat. No. 5,740,128.

For each or a plurality of transmit events, control signals are provided to the transmit beamformer 12 and the receive beamformer 16. The transmit beamformer 12 is caused to fire one or more acoustic lines for each transmit event. As known in the art, the ultrasonic beams or scan lines are focused in one of various formats, such as linear, steered linear, sector, or Vector®.

The excitation signals from the transmit beamformer 12 are provided to the transducer array 14. For imaging pulsatile targets within the subject (e.g., heart or carotid), gating is preferably used to trigger application of the excitation signals to the transducer array 14. In order to further improve three-dimensional imaging, only images corresponding to selected portions of the ECG cycle, the respiratory cycle or both are utilized. Both ECG gating and respiratory gating and triggering are well known in three-dimensional reconstruction of images. See, for example, McCann et al. "Multidimensional Ultrasonic Imaging for Cardiology" at p. 1065. With ECG, gating or triggering, a window is selected a fixed time duration after the ECG pulse maximum. With respiratory gating, it is often simplest to ask the patient to hold his or her breath for the short duration of the ultrasonic scan. Alternatively, chest motion can be recorded using a displacement sensor, and data can be selected for a portion of the respiratory cycle. As yet another alternative, the temperature of air in the patient's nostrils is detected and used as an indication of phase of the respiratory cycle.

Based on the gating or other inputs, the excitation signals are provided to the transducer array 14. The transducer array 14 is of any construction known in the art, such as the one-dimensional, multiple element Acuson 8L5 transducer array discussed above. The elevation aperture of the Acuson 8L5 transducer is fixed and typically not apodized. A plano-concave transducer may be used, such as disclosed in U.S. Pat. Nos. 5,678,544 and 5,438,998. Plano-concave transducers may provide improved elevation beam profiles, resulting in reduced artifacts in the 3D image. For imaging associated with 8 MHz, the elevation aperture may vary from 4 mm in the near field to about 1 mm at the geometric focus (e.g., 18 mm) and then extend to 4 mm or more in the deeper or far field.

One or more of the elements in the transducer array 14 are excited by an excitation signal to produce ultrasonic acoustic waveforms. In particular, the transducer array 14 converts these excitation signals into ultrasonic energy that is directed along transmit beams into the subject, such as the body of a medical patient. Scattering sites within the subject, such as contrast agents or tissue in the subject, cause echo information to be returned to the transducer array 14. This echo information is converted by the transducer array 14 into electrical signals that are applied to the receive beamformer 16.

The receive beamformer 16 is of a construction known in the art, such as an analog or digital receive beamformer capable of processing signals associated with different frequencies. The receive beamformer 16 and the transmit beamformer 12 may comprise a single device. The receive beamformer 16 is caused to generate in phase and quadrature (I and Q) information along one or more scan lines. Alternatively, RF signals may be generated. A complete frame of I and Q information corresponding to a two-dimensional representation (a plurality of scan lines) is preferably acquired before I and Q information for the next frame is acquired (the frames are sequentially acquired).

As known in the art, the electrical signals from the transducer array 14 are delayed, apodized, and summed with other electrical signals to generate the I and Q information. An ongoing stream of summed signals represents the ultrasound beam or line, or portions of the lines when multiple transmit focus depths per line are used, received from the body. The receive beamformer 16 passes the signals to the filter block 18.

The filter block 18 passes information associated with a desired frequency band, such as the fundamental band using fundamental band filter 24 or a harmonic frequency band using the harmonic band filter 26. The filter block 18 may be included as part of the receive beamformer 16. Furthermore, the fundamental band filter 24 and the harmonic band filter 26 preferably comprise one filter that is programmable to pass different frequency bands, such as fundamental, second or third harmonic bands. For example, the filter block 18 demodulates the summed signals to baseband. The demodulation frequency is selected in response to the fundamental center frequency or another frequency, such as a second harmonic center frequency. For example, the transmitted ultrasonic waveforms are transmitted at a 2 MHz center frequency. The summed signals are then demodulated to baseband by shifting by either the fundamental 2 MHz or the second harmonic 4 MHz center frequencies (the demodulation frequency). Other center frequencies may be used, such as intermediate frequencies between the fundamental and harmonic frequencies. Signals associated with frequencies other than near baseband are removed by low pass filtering.

As an alternative or in addition to demodulation, the filter block 18 provides band pass filtering. The signals are demodulated to an intermediate frequency (IF)( e.g., 2 MHz) or not demodulated and a band pass filter is applied. Thus, signals associated with frequencies other than a range of frequencies centered around the desired frequency or an intermediate frequency (IF) are filtered from the summed signals. The demodulated or filtered signal is passed to the signal processor 20 as the complex I and Q signal, but other types of signals, such as RF signals, may be passed.

The signal processor 20 comprises one or more processors for generating two-dimensional Doppler or B-mode information. For example, a B-mode image, a color Doppler velocity image (CDV), a color Doppler energy image (CDE), a Doppler Tissue image (DTI), a Color Doppler Variance image, or combinations thereof may be selected by a user. The signal processor 20 detects the appropriate information for the selected image. Preferably, the signal processor 20 comprises a Doppler processor 28 and a B-mode processor 30. Each of these processors is preferably a digital signal processor and operates as known in the art to detect information. The Doppler processor 28 estimates velocity, variance of velocity and energy (with or without clutter filtering) from the I and Q signals. The B-mode processor 30 generates information representing the intensity of the echo signal associated with the I and Q signals.

The information generated by the signal processor 20 is provided to the scan converter 22. Alternatively, the scan converter 22 includes detection steps as known in the art and described in U.S. application Ser. No. 08/806,922. The scan converter 22 is of a construction known in the art for arranging the output of the signal processor 20 into two-dimensional representations. Preferably, the scan converter 22 outputs video image data frames for display. The frames may be exported in a DICOM Medical industry image standard format or a TIFF format. Thus, the plurality of two-dimensional representations are generated. Each of the representations corresponds to a receive center frequency, such as a second harmonic center frequency, and a type of imaging, such as B-mode. For three-dimensional imaging, the representations may also correspond to elevation positional information.

A. SPECKLE REDUCTION:

After scan conversion, each frame of data is provided to the compounding filter 31. The compounding filter is a digital signal processor, filter, look-up table or other device for performing the filtering discussed below. In alternative embodiments, the compounding filter 31 filters data prior to application to the signal processor 20 (filters RF, IF or baseband I & Q data). In yet other alternative embodiments, the compounding filter 31 filters detected data output from the signal processor 20 and prior to scan conversion.

The compounding filter 31 spatially compounds two or more two-dimensional frames of data. Preferably, the frames of data correspond to parallel scan planes in the elevation dimension with one or more millimeters of spacing between each scan plane (e.g., 0 degree steer in elevation focused at infirmity or some finite range). Other separations (spacing) may be used with or without parallel scan planes (steered at different angles in elevation relative to the range or azimuth dimension with or without intersection).

The spaced two-dimensional frames of data are obtained by translation or rotation of the transducer array 14 (electronically or mechanically) as discussed above. During elevation motion with a spacing of about 1 mm between adjacent scan planes, speckle signals from random scatterers may decorrelate more rapidly than signals from imaged structure. It is hypothesized that signals from imaged structure are not significantly disrupted by small shifts in elevation (relative to the elevation resolution) since the source of the image structure signal is likely represented within each of the spaced two-dimensional frames of data. For example, a 1 mm range of elevation motion using a transducer corresponding to a mean elevation slice thickness of 2 mm (4 mm near and far field and 1 mm at the geometric focus) results in continuity of the imaged structure for a plurality of frames. However, for sources of speckle, slight motions in elevation may be sufficient to change the statistical nature of the echo signal significantly. Thus, spatial compounding may result in reduced speckle due to decorrelation of speckle while allowing imaging of structure (which exhibits little or no decorrelation). Compounding may also be used for non-overlapping data (the spacing between the scan planes is larger than the elevation thickness associated with insonification of each scan plane).

For compounding, the frames of data are preferably aligned in the range and/or azimuth dimensions. To align the frames of data, the relative range and azimuth position of each frame relative to another frame is determined. For example, a position sensor (e.g., magnetic sensor) or a minimum sum of absolute difference (MSAD) calculation is used. The MSAD technique is discussed in U.S. application Ser. No. 08/621,561 (filed Mar. 25, 1996), Ser. No. 08/807,498 (filed Feb. 27, 1997) and Ser. No. 08/916,585 (filed Aug. 22, 1997) to Hossack et al. The relative rotation of the frames of data may also be determined. Based on the positional information, the frames of data are aligned using registers or other suitable memory devices. Alternatively, the frames of data are spatially compounded without alignment in one or both of the range and azimuth dimensions.

In one embodiment, the frames of data are aligned as a function of a region of interest. Image distortion may limit the ability to determine the correlation between two entire frames of data. The user manually selects or the system 10 automatically selects a region of interest. In alternative embodiments the user selects a point, and the system 10 defines a region of interest around or centered on the point. Preferably, the region of interest is at least two times the speckle period in each dimension. The speckle period varies as a function of transducer geometry and frequency. For example, transmitting at a 5 MHz frequency with a transducer having a 4 cm aperture provides a 2 mm wide by 1 mm high speckle period. The speckle period may be measured or estimated as a function of the transducer geometry and frequency. Alternatively, the size of the region of interest is determined as a function of common usages, such as using a 10×10 or 20×10 block of pixels. For efficient processing, a 32×32 or 48×48 pixel area in the middle of the image region may be used for determining an amount of correlation. Other locations within the image, such as at the top or at the bottom of the image or both may be used. Smaller or larger regions of interest, including regions of interest less than two speckle periods wide or high, are possible.

The selected region of interest is used to determine the correlation and corresponding translation in range and/or azimuth and rotation between any two frames of data. Alternatively, the region of interest is emphasized over other regions within the frames of data, such as applying weighted averaging to correlation calculations. A higher weight is applied to the correlation value for the region of interest than to correlation values associated with other regions. The translation and rotation are then determined as a function of the entire image with an emphasis on the region of interest.

In one embodiment, the amount of compounding between any two or more frames of data is determined as a function of the degree of correlation between the two frames of data. The degree of speckle suppression through spatial compounding is a function of the degree of decorrelation between the frames of data.

A plurality of frames of data are acquired as a function of time. The frames of data preferably comprise polar or rectangular coordinate detected acoustic line data, but may comprise incoherent data, in-phase and quadrature, radio frequency scan converted or other ultrasound data. Alternatively, scan converted digital image data (i.e., video data) is used. For each sequentially adjacent or other pair of frames of data, a degree of correlation between the two frames of data is determined.

To determine the degree of correlation between any two frames of data, an indicator of the amount of correlation is determined. Any one of various correlation or cross-correlation functions may be applied. For example, a correlation coefficient is determined from the following equation:

$$\text{Correlation Coefficient} = \sum_{j=1}^{L} \sum_{i=1}^{K} \frac{S_N(i, j) S_{N-1}(i, j)}{S_N(i, j)^2} \quad (1)$$

where L is the number of vertical pixels, K is the number of horizontal pixels, N is the frame number and SN(i,j) is the amplitude of a pixel at the location i, j. In an alternative embodiment, the amount of correlation is determined as a function of a sum of absolute differences as follows:

$$\text{S.A.D.} = \left( \sum_{j=1}^{L} \sum_{i=1}^{K} |S_N(i, j) - S_{N+1}(i, j)| \right) \quad (2)$$

The sum of absolute differences may be normalized as follows:

$$\text{S.A.D Normalized} = \sum_{j=1}^{L} \sum_{i=1}^{K} \frac{|S_N(i, j) - S_{N+1}(i, j)|}{S_N(i, j)} \quad (3)$$

The sum of absolute differences provides an approximate indication of the degree of correlation and is preferably applied when the frames of data have a similar mean intensity. The sum of absolute differences is more computationally efficient than determining the correlation coefficient. Other methods for determining an amount of correlation may be used, such as a user determination based on viewing images associated with the frames of data.

The degree of correlation may be determined as a function of all of the data within the frames of data or as a function of data representing a region of interest within each frame of data. Preferably, the degree of correlation is determined as a function of a region of interest associated with data near the transducer array 14. The signal to noise ratio may be higher adjacent the transducer array 14 than spaced from the transducer array 14. Alternatively or additionally, the degree of correlation is determined before the ultrasound data is compensated for focal gain. The intensity of the acoustic waveforms is highest at the focus and many conventional ultrasound systems compensate for the varied intensity as a function of distance from the focal point. If the signal to noise ratio falls below a noise threshold, a warning is preferably given that the amount of correlation determined may be unreliable. The system 10 may perform compounding regardless of any warning.

The frames of ultrasound data are compounded as a function of the degree of correlation. The degree of correlation is a function of the amount of elevational motion between two frames of data, the point spread function in the range and azimuthal dimensions, the operating frequency, the type of transducer array, the type of ultrasound data and the tissue being imaged. Based on testing of user preferences, a degree of correlation threshold is selected for distinguishing between different amounts of compounding. For example, a correlation coefficient of 0.5 may be sufficiently low that an optimal trade off between speckle reduction and loss of resolution is obtained by providing a particular level of compounding. More than one threshold may be used to determine different amounts of compounding for different degrees of correlation. In alternative embodiments, the user may select one or more degrees of correlation thresholds.

Preferably, a finite impulse response filter is used to provide an average or weighted averaging of any number of frames of data. An infinite impulse response filter is alternatively used. In yet other alternative embodiments, a non-linear function for compounding is used, such as a maximum write function. For a maximum write function, the maximum amplitude value from the same location within the frames of data is output as the compounded data for that location. The maximum write function may provide better resolution of bright targets. Other non-linear functions may be used. For example, amplitude dependent compounding is used. The amount of compounding for each pixel is varied as a function of the pixel amplitude.

If the degree of correlation is low, less compounding may be provided. Where the frames of data are more similar (i.e. a higher degree of correlation), more compounding may provide better speckle reduction than associated with less compounding. Where frames of data are decorrelated, less compounding may provide speckle reduction without loss of resolution. To provide less compounding, any one frame of data is emphasized more in the output compounded frame of data. For example, a greater weighting is applied to. a particular frame of data and/or fewer frames of data are averaged together or compounded. If the degree of correlation is high, a greater amount of compounding is provided. To provide more compounding, any one particular frame of data is emphasized less in the output compounded frame of data. For example, a more similar or the same weighting coefficients are applied to each frame of data and/or a greater number of frames of data are compounded together In one embodiment, the degree of correlation is used to provide an error signal to the user. If the degree of correlation is above an error threshold value indicating little motion between successive frames of data, the user is prompted to rescan.

The degree of correlation between two frames of data are used for determining an amount of compounding associated with one or both of the frames of data. In one embodiment, a sequence of three frames of data (e.g., N−1, N, N+1) is used to determine the amount of compounding. The average degree of correlation between frames (1) N−1 and N and (2) N and N+1 is determined. The average degree of correlation is used for compounding frame of data N. This process is repeated for each frame of data through a sequence of frames, or the average degree of correlation associated with frame N is used for determining an amount of compounding for other frames of data, such as N−1 and N+1. In alternative embodiments, the degree of correlation is determined only for a subset of frames, and the degree correlation associated with other frames is interpolated or extrapolated from the determined degrees of correlation.

The degree of correlation may vary through a sequence of frames of data, indicating a non-uniform translation of the transducer array 14. Preferably, the compounding filter 31 varies the amount of compounding through the sequence as a function of the variance in the degree of correlation. For example, a correlation coefficient of 0.3 is calculated at the beginning of the sequence and 0.7 is calculated at the end of the sequence. The compounding filter 31 compounds a sliding window of every two frames of data at the beginning of the sequence and of every four frames of data at the end of the sequence. Intermediate frames of data may use the same, different, or interpolated coefficients and associated amounts of compounding.

In alternative embodiments, each frame of data is split into subregions and the amount of compounding is varied between each subregion as a function of the degree of correlation associated with each respective subregion. This embodiment is preferably used where each frame of data is associated with the rotation of the transducer array 14 within the elevation dimension.

In one preferred embodiment, the frames of data within the sequence for compounding are aligned in the azimuthal and range dimensions, such as by translation and rotation. By aligning the frames of data, speckle may be reduced through compounding without smearing a target in the resulting image. As discussed above, the alignment is determined as a function of correlation information. Preferably, the alignment correlation calculation is performed prior to the correlation calculation for compounding. The alignment correlation calculation may use the entire frames of data or a region, or regions, of interest as discussed above. First, motion is estimated using a minimum sum of absolute differences or other method for calculating the degree of correlation for alignment. After alignment, the degree of correlation for compounding is calculated using different correlation functions, or the degree of correlation calculated for translation is used for determining an amount of compounding.

In alternative embodiments, the user inputs the amount of compounding. For example, the user selects one of various filters or selects one or more of various filter parameters. The number of frames for compounding (e.g., 3, 5, 7) or the weighting coefficients for compounding (e.g., 0.33, 0.33, 0.33 or 0.20, 0.60, 0.20) or combinations thereof may be selected.

Figure 2:
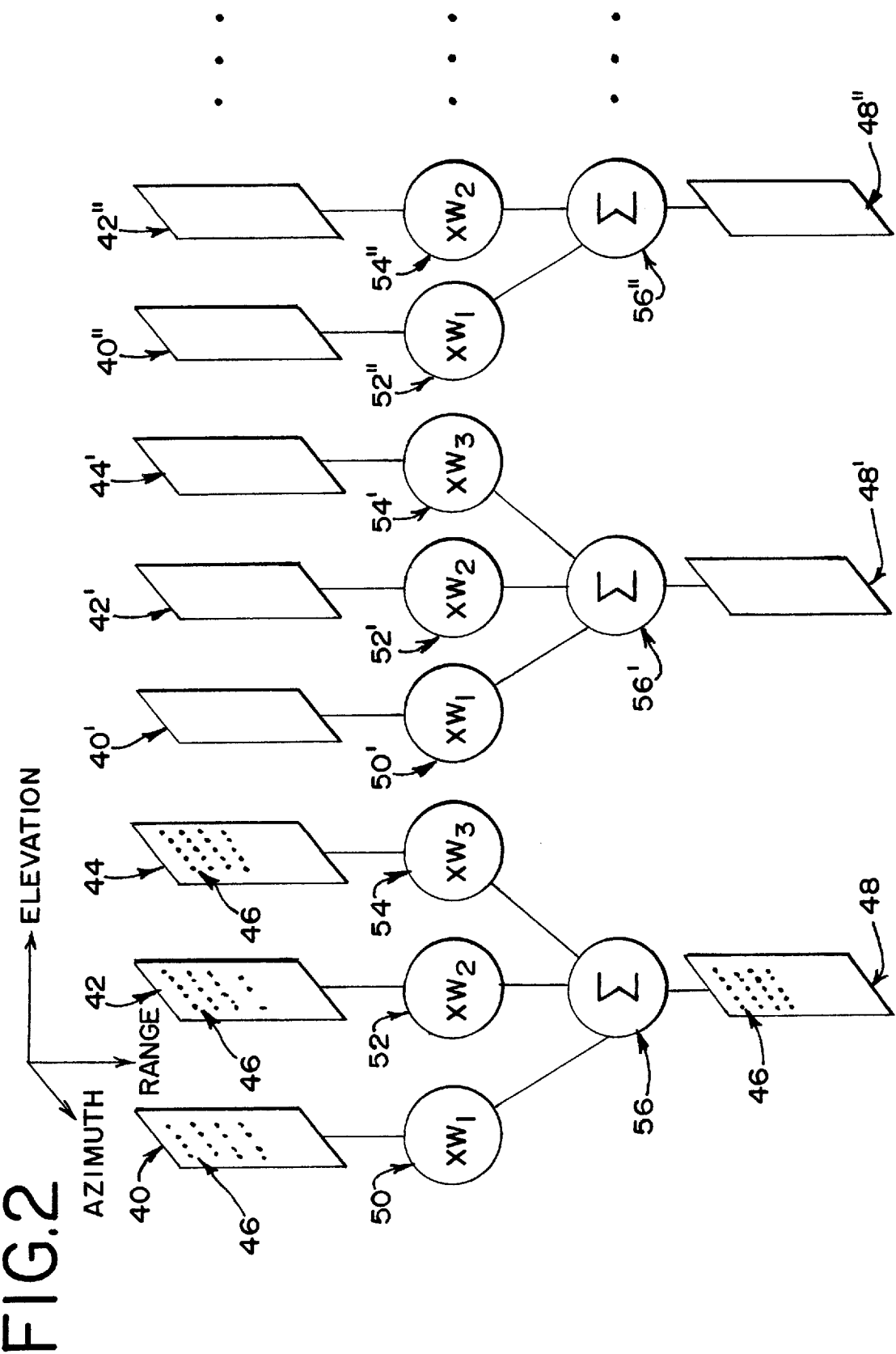
FIG. 2 is a graphic representation of a spatial compounding method for two or three-dimensional imaging.

One form of spatial compounding corresponds to averaging two or more, frames of data. Referring to FIG. 2 and for example, three frames of data 40, 42 and 44 are averaged. Each datum 46 associated with a particular range and azimuth position is multiplied as represented at 50, 52 and 54 by a respective weight $w_1$, $w_2$, and $w_3$. The weighted datum is summed with other data to generate the datum 46 in the compounded frame of data 48. For an average, the weights $w_1$, $w_2$, and $w_3$ correspond to ⅓, or the inverse of the number of frames being compounded. A compounded frame of data 48 is an average of the corresponding data in the input frames of data 40, 42 and 44.

The averaging described above corresponds to low pass filtering in the elevation dimension. Preferably, a finite impulse response (FIR) filter is used. In alternative embodiments, other weighting schemes are applied. For example, five frames of data are weighted with FIR coefficients of 0.2, 0.4, 1.0, 0.4 and 0.2 respectively. Thus, the center frame of data is given the most weighting. Typically, the filter coefficients are normalized so that mean signal level is unchanged. The scaling coefficient applied to the original filter weights ($w_i$) is given by $$\frac{1}{\sum_{i=1}^{N} w_i}$$

In this case (0.2, 0.4, 1.0, 0.4, 0.2), the scaling coefficient is 1/2.2. Other filter coefficients may be used.

Referring to FIG. 1, the spatially compounded frame of data may be used for two-dimensional imaging. Preferably, the spatially compounded frame of data is generated from a plurality of frames of data associated with a 1 or 2 mm elevation sweep (translation) of the transducer array 14.

Preferably, the sweep is electronic with a 1.5 or 2 dimensional array transducer array 14. The frames of data are associated with different scan planes. For example, a 1.5 dimensional array transducer array 14 with 5 elements along the elevation dimension is used (five elevation spaced azimuth linear arrays) as shown in FIG. 9. For a first frame of data, all the azimuth arrays (1, 2, 3, 4, and 5) are excited. All the azimuth arrays are used to receive echo signals. For a second frame of data, three azimuth arrays (e.g., 1, 2, and 3) are excited and a different set of three azimuth arrays (e.g., 3, 4, and 5) receive echo signals. For a third frame of data, a different set of three azimuth arrays (e.g., 3, 4, and 5) are excited and three other azimuth arrays (e.g., 1, 2, and 3) receive echo signals. The three frames of data are compounded, preferably after detection. Alternatively, using the small number of elevation elements, the beam is steered by small angular amounts in the elevation direction. For example, to create beams at −1, 0+1 mm (in elevation) at a range of 40 mm, the beam is steered to −1.43°, 0°, +1.43°. Since the angle being used is slight, the risk of grating lobes due to wide element spacing is reduced. Both the steering angle and the number of active elements may be varied. A change in the number of azimuth elements (N channels) and the number of elevation elements may be used for steering, but may require more channels. Using pure switching, only N channels are used. Generally, switches are cheaper than beamformer channels. As yet another an alternative, a 2 dimensional array transducer is used.

For a one-dimensional array transducer array 14, the transducer array 14 is mechanically scanned in the elevation direction (the linear array is maintained parallel to the azimuth dimension) to generate a spatially compounded two-dimensional image. Preferably, the transducer array 14 moves back and forth in a regular, systematic and quick motion (wobbles). Generally, the range of motion is shorter and the motion is faster than in conventional systems for automatic movement for three-dimensional acquisition. Once a plurality of frames of data are obtained, the frames of data are spatially compounded. Alternatively, the frames of data are temporally persisted by averaging as a function of time, such as by using a infinite impulse response filter. Preferably, each frame of data is associated with scan planes that overlap in the elevation dimension with some or all of the other frames of data due to the elevation focus, as discussed above.

Referring to FIG. 2, a plurality of spatially compounded frames of data 48, 48', 48" . . . are used for three dimensional imaging. For example, a plurality of sets of frames of data (40, 42, 44), (40', 42', 44'), (40", 42" . . . ) are spatially compounded. Other groupings, such as 2, 4 or more frames of data, may be used. Preferably, each frame of data 40, 42, 44 within each set is associated with a scan plane that overlaps, in part, in the elevation dimension with the other scan planes associated with the other frames of data 40, 42, 44 within the set. For example, the overlap corresponds to the elevation focal dimension or focal width. Each frame of data 40, 42, 44 may be associated with a scan plane that overlaps one or a subset of other scan planes associated with the other frames of data. The resulting plurality of spatially compounded frames of data are used for three-dimensional reconstruction as discussed below.

In an alternative embodiment, the frames of data 40, 42, 44, 40' . . . included in a set is a function of a moving window. Thus, a frame of data may be included in more than one set. For example, a window defines three frames of data 40, 42, and 44 in a set and moves by two frames for each set. The first spatially compounded frame of data 48 includes three frames of data 40, 42, 44. The second spatially compounded frame of data 48' includes three frames of data 44, 40', 42' (shifted by two). Other windows or frame selection functions associated with different or varying set sizes or shifting may be used. The resulting plurality of spatially compounded frames of data are used for three-dimensional reconstruction as discussed below.

II. THREE-DIMENSIONAL RECONSTRUCTION

As discussed above, many approaches can be taken in aligning the image data frames to provide the desired three-dimensional reconstruction. Many of the approaches discussed above provide position information associated with the orientation of one image data frame to other image data frames. Referring to FIG. 1, the position information, such as from a rotatable transducer, is provided from the transducer array 14 on a line 32. Alternatively, the position information is calculated off-line or in a processor as discussed in the MULTIPLE ULTRASOUND IMAGE REGISTRATION SYSTEM, METHOD AND TRANSDUCER applications (U.S. application Ser. No. 08/621,561 (filed Mar. 25, 1996), Ser. No. 08/807,498 (filed Feb. 27, 1997) and unassigned (filed herewith:). The position information comprises three components of position (X, Y, Z) and three components of rotation (about X, Y, and Z). Other definitions of position and orientation may be used, such as X, Y, Z information relating to three identifiable points on each 2D image. Furthermore, the position information may be assumed, such as disclosed in Schwartz U.S. Pat. No. 5,474,073.

The position information and the spatially compounded image data frames are provided to a three-dimensional reconstruction computer 34 via a cable or other data link. The 3D reconstruction computer 34 is a remote or internal computer for real time or delayed reconstruction. For example, 3D reconstruction can be performed on a remote workstation such as the AEGIS workstation of Acuson Corporation, the assignee of the present invention. Alternatively, an on-board computer or computer internal to an ultrasound system is used. Preferably, the computer 34 is at least an Intel Pentium® or Pentium II® based PC (200+ MHz or MMX™ 266+MHz) or SGI ($O_2$™ for example) with a memory 36. Preferably, the memory 36 is large, such as 128 MB RAM.

Spatially compounded image data frames can be compressed using any suitable compression technique such as JPEG prior to transfer. After the image data has been received, it is decompressed. Thus, the reconstruction and display of a three dimensional representation is either during the imaging session (real time) or after the imaging session (non-real time).

For reconstruction, the computer 34, using the memory 36, generates information for the three dimensional representation of a volume from the spatially compounded image data frames and appropriate position information. The appropriate position information is selected as a function of the spatial compounding. For example, where three frames of data are spatially compounded, the position information associated with the center frame of data is selected for the compounded frame of data. Alternatively, the position information from all three frames of data used to derive the compounded frame of data is compounded using appropriate weights. Other appropriate position information selections are possible.

Figure 3:
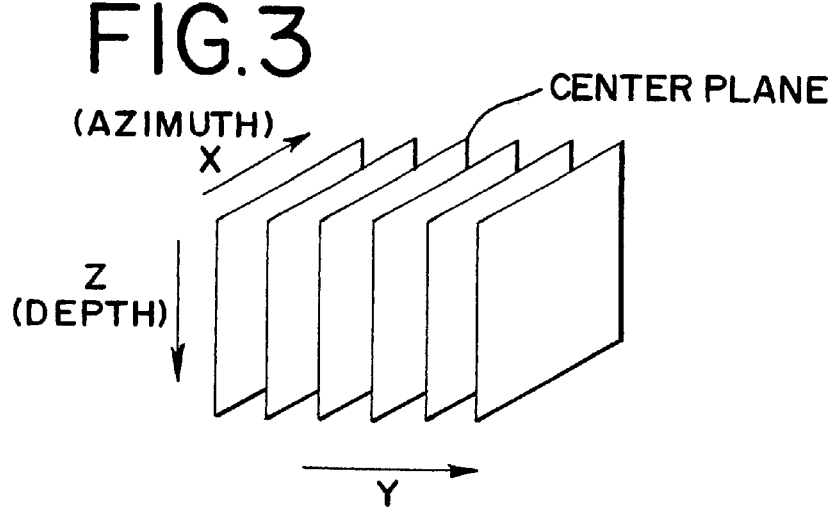
FIGS. 3, 4 and 5 are three schematic perspective views showing a manner in which multiple image data frames can be registered with respect to one another in three-dimensions to form a three-dimensional representation.
Figure 4:
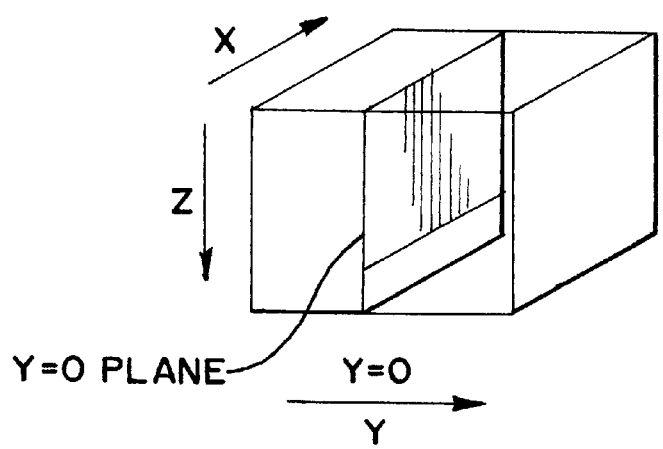
Figure 5:
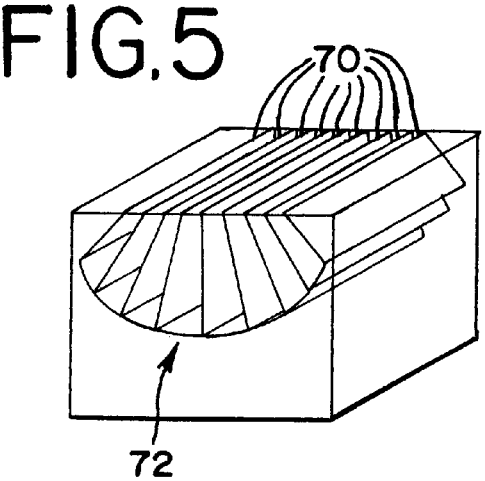

Information from the spatially compounded two-dimensional image data frames is converted to a 3D grid, such as a preferred regularly (equal) spaced volume grid. Equal spacing allows for efficient calculations and use with low cost visualization software. One example is shown schematically in FIGS. 3–5. In this example, the spatially compounded image data frames prior to reconstruction are shown schematically in FIG. 3. The image data frame for a central plane is inserted at a plane aligned with the center of the volume, as shown in FIG. 4. Working outwardly from this center plane, successive image data frames are inserted into their appropriate XYZ locations as a function of the positional information. As shown in FIG. 5, the image data frames are associated with axial rotation about an axis lying in an azimuthal direction along the lens surface of the transducer array 14 (FIG. 1). Other relative positionings are possible.

Once all the frames have been inserted, intermediate points are calculated using three-dimensional linear interpolation techniques relying on the eight closest known data points or other techniques. The computer 34 uses software to construct the 3D representation. Various commercially available software and fixtures are available for 3D reconstruction. For example, TomTec GmbH (Unterschleissheim, Germany) offers software and mechanical fixtures specifically for 3D ultrasound. The software is capable of 3D reconstruction based on several different scan formats, such as rotations and freehand scanning. Life Imaging System Inc. (London, Ontario, Canada) also provides software and mechanical scanning fixtures for 3D ultrasound. VayTek Inc. (Fairfield, Iowa) produces rendering software for a 3D volumetric regularly spaced, orthogonal grid data. As yet another example, Advanced Visual Systems Inc. (Waltham, Mass.) offers an AVS5 software package for constructing and rendering 3D representations from the plurality of image data frames.

Alternatively, the software for reconstruction of the 3D representation is written specifically for the system 10 (FIG. 1) described above. For example, standard language, such as C or C++, is used with WindowsNT® (Microsoft) or a UNIX variant (e.g., Linux) and a graphics Applications Programming Interface (e.g., OpenGL™ (Silicon Graphics Inc.)). Other languages, programs, and computers may be used.

Figure 6:
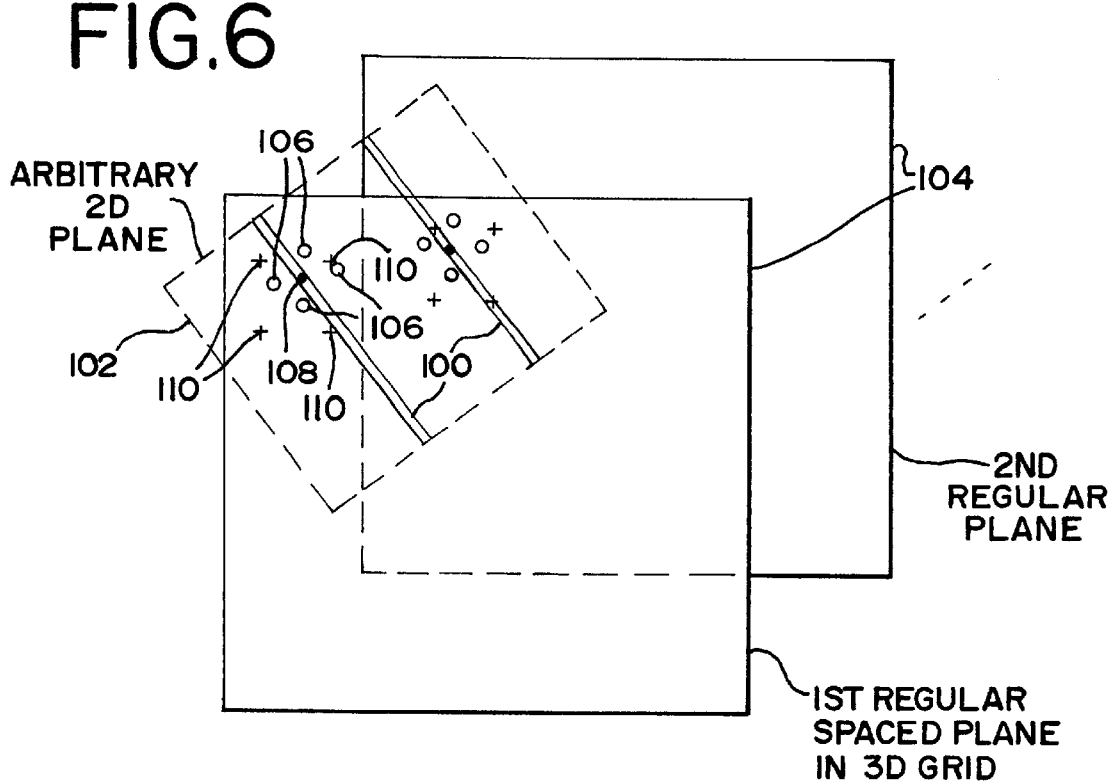
FIGS. 6 and 7 are schematic representations of methods for generating a set of data in a regularly spaced, orthogonal three-dimensional grid.

One approach for generating a 3D data set from arbitrarily spaced image plane data is graphically demonstrated in FIG. 6. Lines 100 corresponding to the intersection between a series of arbitrary planes 102, spaced according to the positional information, and regularly spaced planes 104 of the regularly spaced 3D grid are used. The arbitrary planes 102 may or may not coincide with planes of the 3D grid. Data samples 106 in the arbitrary plane 102 are linearly interpolated with neighboring data samples 106, such as 4 samples, to derive interpolated data samples 108 along the lines 100. A series of interpolated data samples 108 associated with all the regularly spaced planes 104 and the arbitrary planes 102 is obtained. The interpolated data samples 108 are linearly interpolated to generate 3D data samples 110 on the 3D grid. Other methods of interpolation, such as spline fitting, may be used.

Instead of arbitrary planes 104, spaced line data, such as associated with an ultrasound scan line, is used to interpolate to the 3D grid. Thus, the data samples 106 correspond to I and Q or detected data along two or more adjacent scan lines. These data samples are not yet interpolated to the arbitrary two-dimensional planes 102 by scan conversion. Typically, these acoustic data samples 106 are not yet down sampled as is done in scan conversion (such as 16 or more bits of data versus reduced to around 8 bits by the scan-conversion process for compatibility with standard displays). Preferably, the data samples 106 are subjected to a bipolar logarithmic compression function (i.e. log(-x)=-log(x), where x is positive). Preferably, additional samples (e.g., I and Q samples) are interpolated between the known samples (e.g., I and Q samples). To prevent distortion, the phases of adjacent beam data are aligned. For a discussion of this phase alignment, see Method and Apparatus for Coherent Image Formation, Wright et al., U.S. Pat. No. 5,623,928, assigned to the assignee of the present invention.

Figure 7:
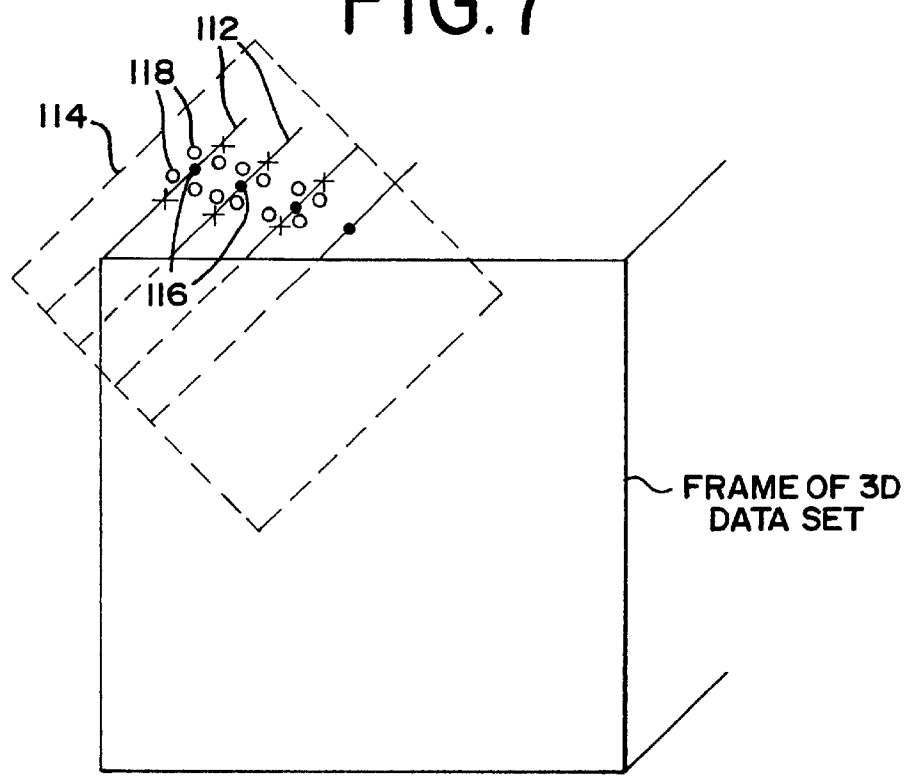

Yet another approach is graphically demonstrated in FIG. 7. A series of parallel lines 112, corresponding to lines within the regularly spaced 3D grid, intersect a series of arbitrary planes 114. At the points of intersection between the lines 112 and the arbitrary planes 114, data samples 116 are interpolated from neighboring image plane data samples 118. Along each line 112, 3D grid data samples are interpolated from the data samples 116. Other approaches to 3D reconstruction may be used, such as a nearest neighbor search (higher speed but inferior spatial accuracy).

The 3D grid of 3D data samples (110 in FIG. 6 and 118 in FIG. 7) obtained by any of the above referenced or other methods may be smoothed or filtered. For example, a known isotropic 3D low pass filter, such as a 3×3×3 FIR filter, or a median filter, such as 3×3×3 or 5×5×5 filters, are used. Alternatively, the line data or image plane data is filtered prior to 3D reconstruction. The three-dimensional reconstruction may include other structures generated by other methods than 3D grid data interpolated from information signals. For example, data associated with a viewing plane selected as the maximum signal along a projection through arbitrary planes as discussed below is used as the three-dimensional reconstruction.

By spatially compounding the frames of data prior to 3D reconstruction, the 3D volume set may be generated more quickly. For example, if there are 200 frames of data spatially compounded prior to reconstruction in sets of 4 frames of data, then 50 frames of data are used to generate the 3D volume set of data. Without prior spatial compounding, all 200 frames of data are used generate the 3D volume set of data. Preferably, the frames of data associated with each set for spatial compounding are associated with scan plane spacing sufficiently close (elevation beam profiles overlap) so that little elevation resolution is lost.

Referring to FIG. 2 and in an alternative embodiment, the frames of data are spatially compounded prior to generating a final 3D volume set using intermediate 3D volume set generation. Independent 3D volume sets of data are derived using every two or more frames of data. For example, every third frame of data 40, 40', 40" is used to generate a first 3D volume set of data. Second and third 3D volume sets of data are generated from other every third groupings of frames of data (e.g., (42, 42', 42" . . . ) (44, 44', 44" . . . ). Other groupings may be used, such as stepping by four or five frames of data to generate four or five 3D volume sets, respectively, selecting frames in response to a moving window function, or any combinations of two or more frames selected in any relationship. Furthermore, spatially compounded frames of data may be used for generation of the 3D volume sets. Preferably, each 3D volume set of data is generated with frames of data positioned closely to frames of data used to generate other 3D volume sets of data.

The 3D volume sets are then spatially averaged. For example, the plane of data associated with a particular elevation or planar position in each 3D volume set is spatially averaged with planes of data associated with the same or a similar elevation or planar position in the other 3D volume sets of data. The averaging is repeated for all similar (within a certain spacing) elevation positions. The result is a single spatially compounded 3D volume set of data. This 3D volume set corresponds to elevation planes positioned, in part, different than at least one of the original 3D volume sets. The spatially compounded 3D volume set of data is the final 3D volume set used for visualization as discussed below.

In an alternative embodiment, a 3D volume set of data is generated with or without any spatial compounding. Once the 3D volume set of data is generated, the data is altered as a function of adjacent data points. Preferably, an anisotropic filter alters the data. For example, anisotropic filters provide for more low pass filtering in the elevation dimension than the range or azimuth dimensions (e.g., 3×5×3 filter). Data along other dimensions are filtered more or less. For example, filtering in one direction only (all pass in other directions) is computed using a one-dimensional filter. See the filtering scheme in appendix A. Anisotropic filtering allows for spatially compounding in the elevation dimension without unnecessary filtering in other dimensions. Combinations of any of anisotropic filtering, spatial compounding 3D volume sets and spatial compounding prior to any 3D volume set generation may be used.

Referring to FIG. 5, if the 3D data set corresponds to a plurality of non-parallel 2D data frames 70 (e.g., 2D data frames at different elevational angles relative to other 2D data frames), the anisotropic filter filters substantially in an elevation dimension with respect to the originally acquired 2D frames. To account for the angular position of the 2D data frames, data at different asimutal and/or range positions within the 3D space are filtered along a substantially elevational dimension (i.e., a substantially elevational line 72 curves in the 3D space to intersect the same position in each 2D data frame). In this example, data representing the lower and forward (i.e., left) most corner of the 2D data frame 70 are filtered substantially elevationally (i.e., filtered along line 72).

III. VISUALIZATION

The 3D volume set of data (3D grid of 3D data samples—110 in FIG. 6 and 118 in FIG. 7) are used for representing a three-dimensional image or for various quantifications. By generating 3D images from spatially compounded 3D volume sets of data, the resulting 3D representation contains less speckle noise effects. No matter how visualized, speckle may be reduced (e.g., a slice or plane at any position through the 3D volume set may contain less speckle noise). Speckle in a two-dimensional image partially obscures the image, but since only a cross-section is being examined, the object is still discernible. For 3D reconstruction, the speckle may surround the object so that the object cannot be discerned. Thus, 3D visualization and quantification using spatially compounding in elevation may result in more useful 3D representations.

Various visualization software, such as Fortner Research LLC's T3D, and techniques may be used to represent the 3D image or reconstruction on a two-dimensional display. Referring to FIG. 1, the computer 34, when operating in a display mode, can select appropriate information from the three-dimensional grid data samples to provide a desired image on a display 38. For example, cross sections can be taken in various planes, including a wide variety of planes selected by the user that do not correspond to the planes of the acquired frames of data. The selected planes are interpolated from the 3D grid data samples. For 3D imaging, the 3D representation on the display 38 may be rotated, zoomed and viewed in perspective as is well known in the art (e.g., Computer Graphics by Foley, van Dam, Feiner and Hughes, Addison Wesley, 1996, chapter 6). Various techniques for 3D imaging are possible, such as surface renderings and volume rendering displays.

For an example of surface rendering, see "MARCHING CUBES: A HIGH RESOLUTION 3D SURFACE CONSTRUCTION ALGORITHM" by W. E. Lorensen and H. E. Cline, Computer Graphics, Vol. 21, No. 4, July 1987. Once the surfaces are determined, a polygon mesh is formed to represent the surface. The surface is rendered with lighting cues, such as Gouraud or Phong shading. Gouraud shading is simpler than Phong shading and may be accelerated with suitable hardware, but Phong shading produces a higher quality image.

By applying a threshold to the data set, such as with the compounding filter 31, the 3D reconstruction computer 34 or another processor, the rendered surface is defined by the user. Thus, the user controls the image displayed or the quantity calculated from the data set.

As an alternative to the surface rendering discussed above, the polygon mesh is derived by applying border detection to each image plane (two-dimensional representation). For example and referring to FIG. 8, a border 124, such as a vessel border, is determined in each appropriate image plane 122 automatically or by user designation with a mouse or other device. For example, the border 124 corresponds to the edges of tissue structure, edges of a chamber or blood filled region (such as with contrast agents), or an edge of an area not filled with blood or a contrast agent (such as unhealthy tissue in the heart muscle). The border 124 may be an enclosed border as shown or may end at another location, such as a user selected location. A data sample 120, such as a first data sample, is associated with a topmost or a beginning detected sample in each image plane 122. In a particular direction, such as clockwise or counterclockwise, the border 124 is divided into a fixed number of points 126 and associated equally spaced segments, such as 50 points. Each segment is in number sequence. The polygon mesh is formed by logically linking the numbered points 126 from image plane to image plane (e.g., Frame #1, point #1 is linked to Frame #2, point #1). The links and the segments define the polygon mesh. Diagonal links may be inserted into the rectangular mesh elements to produce a conventional triangular mesh.

Another technique for representing the 3D data samples on the display 38 is volume rendering, such as alpha blending, maximum intensity or minimum intensity projection. Based on a range of viewing angles, such as 120 degrees, and the incremental values between each viewing angle, such as 1 degree, multiple three dimensional projections are determined, such as 121. Each projection corresponds to a viewing plane that is perpendicular to the viewing angle. The 3D data samples at each viewing angle are summed along the lines of vision or normal "into" the 3D grid or viewing plane. Thus, a value for each region in a viewing plane is determined. For alpha blending, a weighting is applied to each 3D data sample. Typically, each sample is weighted for opacity according to the associated gray scale level. The weighting values may be selected to emphasize near objects. Thus, a sense of front and back regions is created. Alpha blending allows viewing of internal objects relative to surrounding objects. The intensity level associated with each sample may be set as a function of depth, and the translucency associated with each sample may be separately controlled according to an arbitrary or selected function. The intensity and translucency values are combined to generate a display value. Instead of alpha blending, maximum, minimum or other functions may be used. For maximum or minimum intensity projection, the maximum or minimum 3D data sample, respectively, along each line into the viewing plane is used instead of the summation. Other viewing techniques may be used.

The 3D data samples may include information associated with a plurality of processing modes, such as (1) harmonic B-mode information and (2) harmonic or fundamental Doppler information or fundamental B-mode information. For example, the 3D data samples include a harmonic B-mode value and a separate color Doppler velocity value.

A chamber or other object may be visualized as described above, such as a surface rendering, as a function of time. For example, the 3D representation is displayed as a series of images within a heart cycle. This dynamic 3D representation indicates changes in shape and volume over time.

Referring to FIG. 1, for two dimensional imaging, the compounding filter 31 provides the spatially compounded frame of data to the display 38. As known in the art, the scan converted frame of data is used to generate a two-dimensional image on the display 38.

IV. OTHER CONSIDERATIONS:

Other than compounding along the elevation dimension, spatial compounding may be performed along the azimuth and range dimensions. For example, a frame of data is obtained for each of a plurality of scan planes off-set along the azimuth dimension (same elevation position). The frames of data are aligned and spatially compounded. These spatially compounded frames are then processed as discussed above (spatially compounded with frames of data off-set in the elevation dimension) or are used to generate a two or three-dimensional image.

For Doppler images, whether two or three-dimensional, spatial compounding may be used to minimize random Doppler noise. Any of various Doppler modes may be used, such as Doppler energy, velocity, variance, tissue velocity and tissue energy. Signals associated with real flow are retained if the compounded frames of data are associated with overlapping scan planes in the elevation dimension.

Section 2—Enhanced Imaging

Independently of or in addition to the speckle reduction embodiments discussed above, the sets of data may be used for enhanced imaging by combining various types of data. Various types of B-mode or Doppler data are separately converted to regularly spaced data grids (two or three-dimensional). Types of B-mode data include data derived from fundamental or harmonic frequency operation in conjunction with tissue or injected contrast agent and combinations thereof. Types of Doppler data include energy, velocity and variance data derived from measurements of blood flow or tissue motion and combinations thereof. The data is then combined, such as applying a Doppler energy threshold to Doppler velocity data. If the resulting image is not satisfactory to the user, the data is combined again pursuant to a different relationship, such as a different Doppler energy threshold level. Time consuming re-scanning of the patient and time consuming re-computation of the 3D grid data values to apply a different relationship between the data may be avoided.

Generally, the versatile method discussed above is performed by an imaging system with the Doppler Tissue and flow detection processors outputting raw, not combined or incomplete combination, data for storage or three-dimensional reconstruction. For example, raw Doppler data in an acoustic line format is output. Each type of Doppler data is interleaved or processed in parallel with the other types of Doppler data. Position information for three-dimensional imaging is also output with the Doppler data. Thus, various processing and combinations may be made as a function of user input to generate representations of data corresponding to either two or three-dimensions. If the user desires a different process or combination, the same data can be used.

I. ULTRASOUND SYSTEM

Referring now to the figures, and in particular, FIG. 10, a preferred embodiment of an ultrasound system for two and three-dimensional imaging as discussed above is generally shown at 11. The ultrasound system 10 includes a transmit beamformer 12, a transducer array 14, a receive beamformer 16, a system controller 15, a signal processor block 20, and a user interface 17. Remote from the system 11 or included as part of the system 11 are a reconstruction processor 19, a memory 21, a combination processor 23, and a display 38. A three-dimensional rendering processor 25 may also be included. Numerals that are the same in FIG. 10 as in FIG. 1 represent the same or similar components. Components labeled with different numbers in FIG. 10 than in FIG. 1 may comprise different components, different schematic representations of the same components or the same components. For example, the 3D rendering processor 25 and/or the reconstruction processor 19 of FIG. 10 may comprise the 3D reconstruction processor 34 of FIG. 1, the memory 26 of FIG. 10 may comprise the image data storage 36 of FIG. 1, and the combination processor 23 of FIG. 11 may comprise the compounding filter 31 of FIG. 1. Likewise, the image processor 20 of FIG. 10 may comprise the image processor 20 and scan converter 22 of FIG. 1.

The ultrasound system 11 is configurable to acquire information corresponding to a plurality of two-dimensional representations or image planes of a subject for three-dimensional reconstruction or two-dimensional imaging. To generate a two-dimensional representation of the subject during an imaging session, the ultrasound system 11 is configured to transmit, receive and process during a plurality of transmit events. Each transmit event corresponds to firing along an ultrasound scan line in the subject.

The transmission and reception of acoustic energy is performed as discussed above. For this enhanced imaging embodiment, each beam is preferably transmitted with a line focus. The line focus, such as associated with an Axicon lens, distributes the peak energy along the beam and is disclosed in U.S. Pat. No. 5,740,128. Other focal arrangements may be used, such as a point or multi-point focus. Also for this enhanced imaging embodiment, the arrays are preferably 1.5 D or plano-concave for obtaining a fine elevation beam, but other one-dimensional or two-dimensional transducers may be used.

In this embodiment, the signal processor 20 preferably comprises a Doppler flow processor 20A, a Doppler Tissue processor 20B and a B-mode processor 20C. Alternatively, the signal processor 20 includes one or more of only one or two types of processors, additional processor, additional types of processor or fewer processors. Each of these processors is preferably a digital signal processor and operates as known in the art to detect information. The Doppler Tissue and flow processors 20B and 20A may comprise one Doppler processor and a wall filter that outputs interleaved types or a selected type of data. The wall filter filters out low frequency (tissue) signals for Doppler flow processing and performs less filtering to include low frequency tissue signals for Doppler Tissue processing.

The signal processor 20 generates two or more types of data. The types may be selected by a user with the user interface 17, such as a keyboard, analog potentiometers or dedicated switches. In response to the selection, the system controller 15 provides control signals to the signal processor 20. Preferably, the various selected types of data represent substantially the same two or three-dimensional region of the patient. Alternatively, the selected types of data represent different regions, such as elevationally spaced regions.

The Doppler flow processor 20A estimates three types of data, such as Doppler flow velocity, flow variance of velocity and flow energy from the I and Q signals. The Doppler Tissue processor 20B also estimates three types of data, such as Doppler tissue velocity, tissue variance of velocity and tissue energy from the I and Q signals. Preferably, each of these types of Doppler data is independent of the other types. For example, the Doppler velocity data is not adjusted as a function of a Doppler energy threshold. Alternatively, only limited processing, such as default low energy threshold levels, are applied to other data. User input, as discussed below, is used to apply any further or higher threshold or other combination levels.

The B-mode processor 20C generates information representing the intensity of the echo signal associated with the I and Q signals. In this embodiment, the intensity information includes two or more types of B-mode information, such as fundamental and harmonic frequency based information or low pass and all pass filtered information. Separate transmit firings may be used for each line of B-mode intensity harmonic and fundamental information. Alternatively, separate receive beamformers for each frequency band are used to obtain data from the same transmit firing. Preferably, the fundamental and harmonic lines are fired alternately. Alternatively, the firings are interleaved by frame. In either case, substantially the same region is scanned. The term "substantially" is used to account for unintentional movement of the transducer relative to the patient.

For B-mode harmonic and fundamental interleaved data, the scan converter within the image processor 20 preferably includes an extended buffer. Typical scan converters include a buffer for storing two lines of data. Two successive lines of data are used for scan conversion. Since the fundamental and harmonic lines are interleaved, the extended buffer stores two lines of fundamental and two lines of harmonic data. A plurality of lines of harmonic information are scan converted into one frame of data, and multiple lines of fundamental information are scan converted into another frame of data. Both frames of data represent substantially the same region of the patient.

II. RECONSTRUCTION

Figure 11:
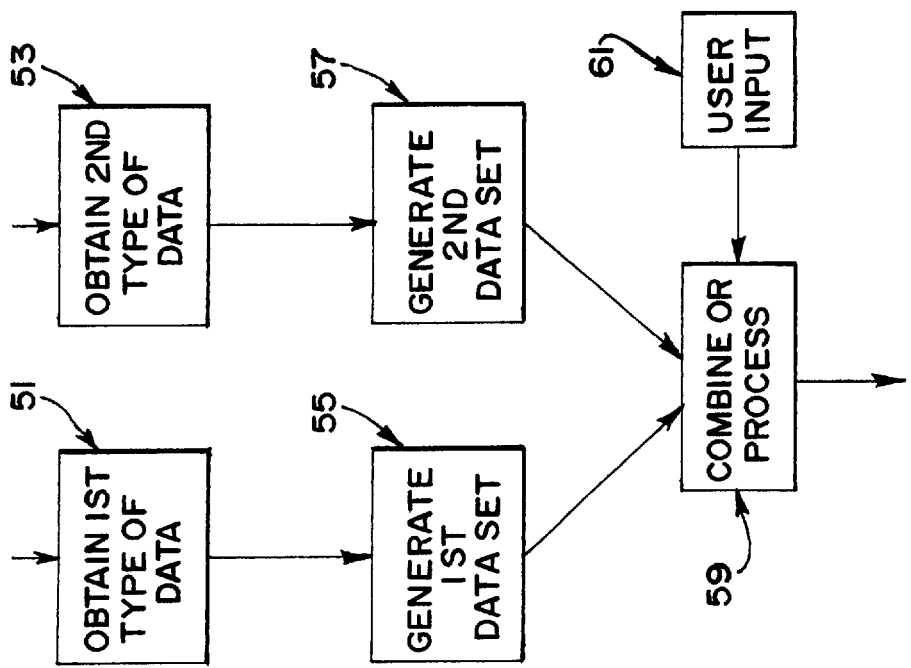
FIG. 11 is a schematic representation of one embodiment of a method for generating a two or three-dimensional representation.

The scan converted information generated by the signal processor 20 is provided to the reconstruction processor 19. As an alternative to including the scan converter in the signal processor 20, the reconstruction processor 19 includes the scan converter. For example, line data is provided to the reconstruction processor 19 for three-dimensional imaging. For two-dimensional imaging, the reconstruction processor 19 preferably comprises the scan converter. Preferably, the data provided to the reconstruction processor 19 is raw data or data associated with little or no thresholding or other post acquisition or post-detection processing, such as temporal persistence. As represented in FIG. 11, the process obtains data (e.g., frames of data) associated with at least two different types of data (e.g., Doppler flow velocity, Doppler Tissue variance, B-mode harmonic) and substantially the same region of a patient in steps 51, 53.

Using the frames of data and positional information, the reconstruction processor 19 generates at least two data sets representing three dimensions (3D data sets or reconstructions). Referring to FIG. 11, these data sets are generated in steps 55, 57. Each data set preferably corresponds to a particular type of data. Preferably, each datum in the data set comprises an 8 or 16 bit value, such as the value output by scan converters or a transform used for compression (e.g., JPEG data). Alternatively, other bit sizes or data formats may be used. Alternatively, two-dimensional frames of data or data sets are generated.

Since two or more 3D data sets are generated for two or more respective types of data, the same interpolation factors are preferably applied for each 3D data set. Each frame of data for each type of data, such as Doppler velocity and Doppler energy, corresponds to the same positional information (substantially the same region of the patient). To save computation bandwidth, the same floating point interpolation factors are applied to each of the various types of data.

Using the processes discussed above, a plurality of two or three-dimensional data sets are generated. For example, data sets of Doppler velocity, Doppler energy and fundamental B-mode are generated. Data sets of other types of data and more or fewer data sets may be generated. Additionally, a plurality of data sets of the same type of data differentiated by time may also be generated. Preferably, the type of data for each data set is selected by the user. For example, using the user interface 17, the user selects 3D Doppler velocity, Doppler energy and harmonic B-mode data sets. The system controller 15 receives the input and provides appropriate control data to the reconstruction processor 19 and the memory 21.

The memory 21 is controlled to allocate an appropriate amount of storage for each of the data sets. If 128 MB of memory is available, the user may choose among various allocations of memory, e.g., 128 MB to B-mode; or 64 MB for B-mode and 64 MB for Doppler energy; or 32 MB for B-mode, 32 MB for Doppler energy, 32 MB for Doppler variance and 32 MB for Doppler velocity; or 64 MB for Doppler velocity and 64 MB for Doppler energy. Other allocations are possible using more or less available memory. By selecting fewer types of data, more time differentiated or larger sets of data may be generated. Alternatively, the data sets are not stored in the memory 21 and are passed to a combination processor 23.

III. COMBINATION

Data sets, whether stored or not, are passed to the combination processor 23. Preferably, the combination processor 23 comprises the reconstruction processor 19 operating pursuant to different software. Alternatively, the combination processor 23 comprises a different processor or dedicated circuitry, such as one or more look-up tables.

In addition to receiving the data sets, the combination processor receives control signals from the system controller 15. The control signals are based on user input from the user interface 17 and indicate user selection of one or more of various relationships. The relationships, assigned by the system controller 15 or the combination processor 23, control combination of the data sets. Referring to FIG. 11, a combine or process block 59 combines or processes the data sets pursuant to input from a user input block 61.

The relationships include selection or setting for each data set of: hues (color maps), opacities, weights, thresholds and mixing functions. For a first example, different or the same opacity and/or hue levels are set for each of two or more data sets, such as a Doppler velocity 3D data set and a Doppler energy 3D data set. Thus, the Doppler velocity data may be associated with a lesser opacity than the Doppler energy data. Alternatively, opacity levels associated with data representing a 3D volume are controlled as a function of a Doppler parameter, such as Doppler velocity data modulating the opacity of Doppler energy or velocity data. By controlling the opacity level, some data is more opaque than other data. The resulting display representing the 3D volume emphasizes opaque regions as compared to more transparent regions. Areas of clinical interest, such as a leak in a heart valve or other high variance or velocity jet, are emphasized.

As a second example of combination, one data set, such as a Doppler energy 3D data set, is used to threshold another data set, such as a Doppler velocity 3D data set. For example, only Doppler velocity values associated with Doppler energy values (same spatial position) above or below a certain level are passed from the combination processor 23 (FIG. 1). As a third example, two data sets are mixed in response to a function, such as averaging, adding (X+Y), weighted adding (wX+(1−w)Y), multiplying (X×Y), subtracting (X−Y), dividing (X/Y) or other mixing functions, where w is a weight coefficient (e.g., in the range of 0 to 1). For example, normalized variance (i.e., variance/power) is provided with a division mixing function. In each case, the combined valves of the two data sets correspond to substantially the same spatial location in the imaged tissue. Combinations corresponding to multiple spatial locations may be used, such as the calculation of shear (i.e., difference in velocity between spatial locations). Other mixing functions include combinations disclosed in U.S. Pat. No. 5,479,926 to Ustuner (look-up table for combining filtered and unfiltered B-mode intensity data), the disclosure of which is herein incorporated by reference. For a fourth example, two or more data sets, such as two-dimensional data sets, are used as inputs to a selected one of several color maps. Other relationships are possible.

Referring to FIG. 1, the combination processor 23 combines the data sets based on the selected relationship. As used herein, combination includes inputting two or more data sets and outputting one or more data sets and includes inputting two or more data sets and outputting the same number of data sets where at least one data set is altered with respect to another data set (e.g., setting the intensity, hue or opacity of one data set relative to another data set). To perform the combination, the combination processor 23 operates pursuant to the assigned relationship. In the examples above: (1) the hue or opacity of each datum for one or more data sets is set higher or lower; (2) one data set is converted into 0 and 1 values (a mask) as a function of a threshold, and multiplied with another data set; (3) spatially associated data from two or more data sets are preferably input to a two-dimensional look-up table corresponding to the appropriate mixing function; and (4) spatially associated data from two or more data sets are preferably input to a two-dimensional look-up table corresponding to the appropriate color map. Other processes for combination may be used. For example, Doppler energy and velocity or Doppler variance and Doppler Tissue velocity data sets are combined using the method disclosed in U.S. application Ser. No. 08/827,863, filed Apr. 19, 1997 for Adaptive Temporal Filtering To Enhance Fluid Flow Tissue Motion Imaging. For three-dimensional imaging, color map assignment or combination is preferably performed after the rendering process discussed below.

Furthermore, other processes may be performed by the combination processor 23, including processes selected by the user on the user interface 17. For example, a Doppler velocity threshold is applied to a Doppler velocity data set. As another example, the sign associated with Doppler velocity data is eliminated (a value of −50 becomes +50) so that non-directional Doppler velocity remains. Various other parameters, such a hues or opacities, may be set for a combined data set. Other processing may include filtering. The data set or sets are smoothed or filtered prior to or after any other combination or other processing. For example, a 3D low pass filter, such as a 3×3×3 FIR filter, or a median filter, such as 3×3×3 or 5×5×5 filters, are used. Filtering may include a combination relationship selection. For example, different filters are selected for application to different data sets. Alternatively, the line data or image plane data is filtered prior to 3D reconstruction.

IV. VISUALIZATION

For two-dimensional imaging, the data set output by the combination processor 23 is provided to the display 38. The display 38 comprises a CRT monitor or other display device for generating images.

For three-dimensional imaging, the data set output by the combination processor 23 is rendered into a three-dimensional representation by the 3D render processor 25. The 3D render processor 25 may comprise the same processor as the combination processor 23 and/or the reconstruction processor 19. Alternatively, a separate processor is used for rendering.

3D data sets, combined or not combined, or the volume rendering data are also or independently used to calculate various quantities, such as a volume. For example, based on border detection, such as discussed above for surface rendering, or based on selection of a region of interest by the user, the volume of a chamber (surface bounded or region of interest bounded volume) is calculated. The volumetric elements, such as voxels, within the surface or region are summed. The sum is multiplied by a volume associated with each volumetric element. Other quantities may be calculated. For example, the volume is calculated as a function of time. This time based information is displayed as a series of quantities or as a waveform (graph of volume as a function of time). As another example, a ratio of the volume change over a heart cycle to the maximum volume over the same heart cycle is determined. The ratio of heart chamber volume change (left ventricle) to maximum chamber volume provides an ejection fraction and is a quantity used in the assessment of heart health. The ratio may then be determined as a function of time or a mean value over a plurality of heart cycles. Any of the quantities may be determined during or after an imaging session.

Other quantities determined from the 3D grid data or surface rendering data include the thickness and volume of the heart muscle. A surface mesh or rendering is produced of the outer and inner surfaces of a heart chamber. Using the 3D location of both surfaces relative to each other, the thickness is determined at any of various locations. The volume of the heart muscle, the difference in volume associated with the inner surface and the volume associated with the outer surface, may also be calculated. The change in thickness or difference in volumes as a function of time may also be determined. A discussion of heart wall measurements is found in Sheehan, U.S. Pat. No. 5,435,310.

Various quantities corresponding to three-dimensional space, such as volume, may also be quantified without constructing the 3D representation or 3D grid data discussed above. Thus, the image plane data or line data output from the signal processor 20 (FIG. 10) is used to calculate the quantity, such as volume. The border or surface is automatically determined based on signal level or manually determined. For example, automatic border detection determines the border or surface based on a threshold value (e.g., median or mean value). One such automatic border detection used in the presence of ultrasound speckle as applied to the 2D planes is disclosed by H. E. Melton, Jr. and D. J. Skorton in "REAL-TIME AUTOMATIC BOUNDARY DETECTION IN ECHOCARDIOGRAPHY", 1992 Ultrasonics Symposium, p 1113–17.

As another example, the polygon mesh surface rendering technique using border detection on image plane data discussed above is used to define the 3D border without reconstruction of the 3D representation or grid data. Assuming the image planes are generally parallel, the volume of each plane is determined. The sum of the pixel areas or data within the border for each image plane is multiplied by a plane thickness to obtain plane volume. The results of each multiplication are integrated over all the image planes (Simpson's Integration) to find the total volume of the region.

Figure 12:
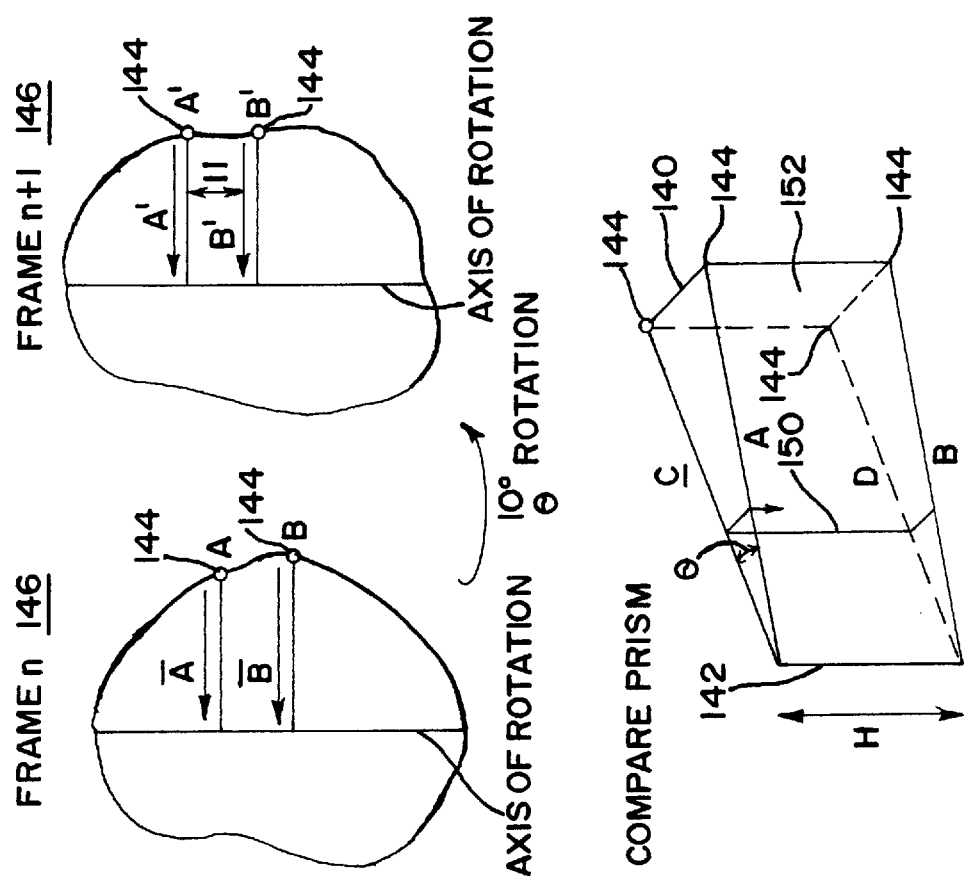
FIG. 12 is a schematic representation of a method for calculating a volume from data representing three-dimensions.

Referring to FIG. 12, if the image planes were acquired using a rotatable transducer (planes not parallel), then the volume is split into prism shaped volumetric elements 140. The axis of rotation 142 is treated as a vertical line of the element 140. A length, L, is calculated as the geometric mean length between the axis 142 and four ranges 144 associated with the border in two adjacent image planes 146. $L=4\sqrt{ABCD}$, where A and C are in one image plane and B and D are in another. The angle, $\theta$, between the image planes is based on the known positional information. The height, H, of each element 140 is the known distance between two adjacent scan lines within an image plane. The volume of each prism is $1/2 L^2 H \sin\theta$. The total volume within the 3D border or surface is the sum of the component prism volumes. This calculation assumes the border is intersected by the axis of rotation. If the axis of rotation is outside the border detected region, the volume of the prism extending from the axis to a "nearer" surface 150 is subtracted from the volume of the prism extending from the axis to "further" surface 152.

Another method for visualizing includes both two and three-dimensional imaging. Referring to FIGS. 13A–D, images 200 comprising a 3D representation 202 and a two-dimensional (2D) representation 204 are displayed. In a preferred embodiment, the 3D representation 202 is generated from a Doppler three-dimensional data set (e.g., velocity, power, variance or a combination thereof), and the 2D representation 204 is generated from a B-mode three-dimensional data set (e.g., harmonic or fundamental frequency processed B-mode data). In alternative embodiments, each of the 2D and 3D representations 204 and 202 corresponds to any of the various types of data discussed above. Various other processing may be performed with either of the data sets, such as persistence or ECG triggering of the Doppler data to smooth out pulsatility. The 2D representation 204 may be generated from a two-dimensional data set.

The 3D representation 202 is generated in any of the various formats discussed above, such as surface rendering or volume rendering. A volume rendering includes accounting for multiple voxels in the depth direction (e.g., alpha blending or maximum intensity projection). The 2D representation 204 is generated as a plane within the three-dimensional data set. The plane may be at any position, such as normal to the viewing angle associated with the 3D representation 202 at a user selected depth. Using interpolation or other techniques, data corresponding to the intersection of the plane with the three-dimensional data set is generated.

The 2D and 3D representations 204 and 202 are combined using either programmed or user selected relationship information. For example, the relative opacity is used to determine any portions of the representations for display. Referring to FIGS. 13A and 13D, the 2D representation 204 is generally translucent. A portion 206 of the 3D representation 202 covered by the 2D representation 204 is still visible. In FIG. 13A, a portion 208 of the 3D representation 202 is generally translucent, allowing the entire 2D representation 204 to be viewed. Conversely, in FIG. 13D, the portion 208 is opaque. Preferably, the opacity of the B-mode 2D representation 204 is a function of the gray scale level (e.g., black has zero or near zero opacity and white has high opacity). When the 2D representation 204 overlies the 3D representation 202 (e.g., red Doppler image), the associated pixels are modified by a whitening effect (e.g., red becomes pink). When RGB values are used for color coding the gray scale and Doppler data, the resulting RGB value for each pixel is a weighted sum of the RGB values for the gray scale and Doppler data. Typically, the gray scale data has approximately equal levels of R, G, and B, and the Doppler data may have larger R values than G and B values. As the gray scale and Doppler data are mixed, the G and B values may have similar values slightly lower than the R value. If the B-mode 2D representation 204 is black, the color of the pixel preferably does not change.

As another example of combining pursuant to a relationship, the visible portions 206 and 208 of the 2D and 3D representation 204 and 202 are determined. Depending on the location of the two-dimensional representation 204 within the scanned region and the viewing angle relative to the scanned region, different portions of the three-dimensional representation 202 are not visible, visible with the two-dimensional representation 204 or block the two-dimensional representation 204.

Various methods of combination may be used. For an alpha blended 3D representation, the accumulated display value is coded in depth until the intersection with an opaque 2D representation. Preferably, an opaque surface polygon rendered 3D representation 202 is defined using OpenGL commands or other Application Programming Interface commands. Z-buffer hardware or software may allow for quick determination whether to show or not show data based on depth and position. The 2D representation may comprise a single polygon with a texture map representative of the 2D image or multiple small polygons, each associated with a color.

Referring to FIG. 14, a method for combining opaque 2D and 3D representations is shown. In step 210, the user inputs a position of the 2D representation within the scanned region. An equation defining Z-depth as a function of X, Y position on the display is calculated in step 212. In step 214, the color for each pixel is set to a gray scale.

For each X,Y location (pixel), Z is reset to 0 in step 216. Z is incremented from the viewer going into the data set in step 218. If a color value is associated with the Z increment as determined in step 220, the incremental Z value is compared with the Z value of the 2D representation in step 222. If the incremental Z value with an associated color value is in front of the 2D representation, the color value opacity at the location is accumulated or stored in step 224. If the incremental Z value with an associated color value is behind the 2D representation, a check for completion is performed in step 226, otherwise the next X,Y location is examined in step 216. If a color value is not associated with the Z increment as determined in step 220, the Z increment is checked against a limit corresponding to the maximum depth in step 228. After accumulation is step 224, step 228 is also performed. If the Z value is within the maximum value, then the process returns to step 218 for the next incremental Z value. If the Z value is larger than the maximum, step 226 is performed to either increment to the next X,Y location or finish the process in step 230.

Preferably, the user selects or changes the various relationships and other image variables. For example, the user selects the opacity for each representation. As another example and referring to FIG. 10, the user changes the position of the 2D representation 204 within the scanned region (i.e., the three-dimensional data set). The user may move the 2D representation 204 forwards, backwards or as a rotation relative to the 3D representation 202. Furthermore, the user may translate or rotate one or both of the 2D and 3D representations 204 and 202 (e.g., change the viewing angle). As yet another example, the brightness or other display characteristics of one or both representations is selected or varied by the user. The user may also cause only one representation to be displayed or the display of additional representations. For example and after displaying both representations overlaying each other or side by side, the user selects the display of only one representation. Since the data sets are stored separately, the remaining display represents the scanned region without information from other data (i.e., no black holes).

By generating an image comprising both 2D and 3D representations 204 and 202, useful information may be isolated. For example, a Doppler 3D representation may show a constriction (e.g., narrowing in the image). Using a B-mode 2D representation, the user may establish whether the narrowing is due to the shape of the vessel wall or weakly echogenic congealed blood. B-mode 3D representations may cloud the displayed image with non-useful information and obstruct structure. Various imaging applications may benefit from 2D and 3D representations in the same image, such as visualizing placenta flow, suspicious blood flow patterns in breasts and general vascular imaging. Furthermore, by capturing and processing B-mode and Doppler information separately, one or both may be selected for display at any point.

V. ENHANCED IMAGING CONCLUSION

Once any of the quantities or images generated from the data sets are displayed, the user may desire to alter the generation of the quantities or images. Since the data sets are first formatted into two and three-dimensional data sets with minimal combination and other processing and separately stored, new quantities and images responsive to changed user selections, such as relationships or other processing, are generated without re-scanning the patient or generating new data sets. The combination processor 23 applies the newly selected relationship or other processing to the appropriate data set or sets. Another image or quantity is then determined from the processed data set or sets. For example, by setting a weight between Doppler velocity and Doppler energy data for combination by weighted summation mixing, the relative emphasis on Doppler energy or velocity data is altered.

Section 3—Adjustable Persistence

Providing adjustable persistence may allow a user to isolate diagnostic information. Temporal and spatial persistence in conventional systems is typically performed before storage of detected or scan converted data in a memory for CINE playback or other memory. During replay, the user cannot vary the level of persistence from that used during acquisition. By allowing the user to vary persistence between two or more frames of ultrasound data after storage in a memory, more versatility for diagnostic analysis is provided. Furthermore, using a finite impulse response filter for applying persistence or compounding may provide even greater flexibility. A FIR filter allows control over the number of filter coefficients and the coefficient values. A FIR filter, such as used for persistence, frequently allows control over a single filter parameter.

I. ULTRASOUND SYSTEM

Referring now to FIG. 15, a preferred embodiment of an ultrasound system for two and three-dimensional imaging allowing adjustable persistence is generally shown at 304. The ultrasound system 304 includes a transmit beamformer 12, a transducer array 14, a receive beamformer 16, a filter 18, a signal processor 20, a scan converter 22, a memory 300, a compounding processor 302, and a display 38. Numerals that are the same in FIG. 15 as in FIGS. 1 and 10 represent the same or similar components. Components labeled with different numbers in FIG. 15 and FIG. 1 or 10 may comprise different components, different schematic representations of the same components or the same components. For example, the memory 300 of FIG. 15 may comprise the image data storage of FIG. 1 or the memory 21 of FIG. 10. The compounding processor 302 of FIG. 15 may comprise the compounding filter 31 of FIG. 1 or the combination processor 23 of FIG. 10.

Like the systems discussed above with respect FIGS. 1 and 10, the ultrasound system 304 of FIG. 15 is configurable to acquire information corresponding to a plurality of two-dimensional representations or image planes of a subject for three-dimensional reconstruction or two-dimensional imaging. To generate a two-dimensional representation of the subject during an imaging session, the ultrasound system 304 is configured to transmit, receive and process during a plurality of transmit events. Each transmit event corresponds to firing along an ultrasound line in a subject.

The transmission and reception of acoustic energy is performed as discussed above with regard to FIGS. 1 and 10. Preferably, a one-dimensional array is used to acquire the frames of ultrasound data. Information is isolated around a harmonic or fundamental of the transmit frequency or at an intermediate frequency by the filter 18. The image processor 20 detects and outputs B-mode and/or Doppler information to the scan converter 22. The output of the scan converter 22 is provided to the memory 300.

The memory 300 comprises any one of various memories, such as a RAM memory, a disk memory, or a tape memory. In one embodiment, the memory 300 is internal to the ultrasound system 304, such as a memory for CINE playback. A CINE memory stores recently acquired images in a loop. In conventional systems, the acquisition and processing parameters (e.g., persistence or gray scale mapping curve) of the stored data typically may not be changed. In alternative embodiments, the memory 300 is provided between the image processor 20 and the scan converter 22 or at another location in the system 304. In other embodiments, the memory 300 is remote from the ultrasound system 304, such as a memory associated with the Aegis® workstation manufactured by Acuson Corporation or another workstation.

The frames of ultrasound data are stored separately in the memory 300. The separate frames of data may be associated with different amounts of processing, such as no spatial or temporal compounding, some spatial and/or temporal compounding and other levels of other processes.

Typically, data for CINE playback is associated with uncompressed ultrasound data formatted along acoustic lines, so frames of data for a few seconds worth of imaging are provided. Remote memories, such as associated with remote workstations, typically store compressed ultrasound data, such as associated with JPEG compression. Frames of data for one minute or more of imaging may be separately stored. Preferably, three or more frames of ultrasound data are separately stored.

The compounding processor 302 is operable to access the memory 300. The compounding processor comprises a digital signal processor or a general processor with software for performing compounding as discussed below. The compounding processor 302 may be internal to the ultrasound system 304, such as a dedicated processor or a general purpose control processor. Alternatively, the compounding processor is remote from the ultrasound system 304, such as an Aegis® workstation or other remote workstation processor. The compounding processor 302 may be in series with the rest of the ultrasound system 304.

II. ADJUSTABLE PERSISTENCE

The compounding processor 302 accesses the memory 300 for providing adjustable combination of frames of ultrasound data saved within the memory 300. Two or more frames of ultrasound data are acquired and stored as discussed above. The frames of ultrasound data stored in the memory 31 comprise a sequence of frames of ultrasound data. The sequence of frames of ultrasound data may be used for non-real time processing, such as during CINE playback or Aegis® remote workstation review or replay. Various levels of persistence or compounding may be provided during replay of frames of ultrasound data from the memory 300. Since a sequence of frames of data are stored, including frames of data acquired before and after any one frame of data, non-recursive processing or compounding may be provided.

In one embodiment, the frames of ultrasound data within the sequence are spaced in the elevation dimension as discussed above for spatial compounding. In alternative embodiments, the frames of data in the sequence represent substantially the same region of a target for use with the temporal compounding. Spatial compounding may include temporal compounding, since each elevationally spaced frame of ultrasound data may be acquired at different times. Likewise, temporal compounding may include elevationally compounding since sequentially acquired frames of data may be associated with different transducer positions, whether intentional or unintentional.

The compounding processor 302 obtains two or more of the frames of data from the memory 300 for compounding. As discussed above, the frames are preferably aligned in range and/or azimuth as a function of translation and rotation. In one embodiment, a region of interest may be selected and used for performing the correlation analysis for alignment. In alternative embodiments, the frames of data are not aligned.

The compounding processor 302 combines the frames of data as discussed above. Preferably, a non-recursive finite impulse response filter (FIR filter) is used for combining the frames of data. In alternative embodiments, a recursive infinite impulse response filter (IIR filter) is used. The number of frames of data compounded together, such as in non-recursive processing, may be selected automatically or as a function of user input. Likewise, one or more filter coefficients, such as two or more weights non-recursively applied to various frames of data or one weight recursively applied, may be selected as a function of user input or automatically. In one embodiment, a FIR filter with normalized weights is used, such as using equal weights for each frame of ultrasound data. The system 304 or user then selects the number of frames compounded together.

In alternative embodiments, the compounding processor 302 applies non-linear combinations, such as combination using a lookup table for implementing the maximum write function discussed above.

The frames of ultrasound data are combined either in real time or as part of a review. For non-real time review combination, 200 or more milliseconds may pass between the storage of frames of data and the combination of frames of ultrasound data. Non-real time processing may allow for non-recursive filtering and combination. For real time processing, a delay associated with acquisition of one or more additional frames may be used to implement FIR filtering.

A plurality of compounded frames of ultrasound data may be output, each compounded frame of ultrasound data associated with the generation of an image, whether sequentially displayed for movement or individually displayed for diagnosis. Each compounded frame of ultrasound data within a set is preferably compounded as a function of a unique set of frames of ultrasound data. For example, each compounded frame of ultrasound data is compounded with a certain number of frames acquired prior to and after a frame of interest. A single compounded frame of data (i.e. static image) derived from a plurality of frames of data may be output by the compounding processor 302.

The output from the compounding processor 302 is used to generate an image or images on the display 38. The output may also be stored in the memory. In one embodiment, the output comprises data in a polar coordinate format, so the scan converter 22 generates the images on the display 38. In other embodiments, the compounding processor 302 outputs frames of data in Cartesian coordinate format. Furthermore, the compounding processor 302 may output data in an uncompressed or a compressed format as discussed below.

After the display of a single or a series of images, the user may adjust the compounding. The user enters additional compounding information, such as a greater or lesser amount of compounding. The user may enter any of various parameters (e.g., a filter type (FIR, IIR), weights, and/or a number of frames) discussed herein. Based on the additional compounding information input by the user, two or more frames of ultrasound data stored in the memory 300 are compounded. The resulting compounded frame of data is used to generate an image on the display 38. Since the sequence of frames of data are stored in the memory 300 separately, the user may adjust the amount or type of compounding to isolate diagnostic information in the image or series of images. If one combination is unsatisfactory, a different combination of the frames of ultrasound data is performed, providing the user with retrospective temporal or spatial persistence. If the transducer is translated in elevation, temporal persistence also provides spatial persistence.

In addition to retrospective compounding, other retrospective processing is provided in one embodiment. The user or the system 304 selects alteration information, such as associated with additional compounding information, contrast enhancement information, gray scale or color mapping functions or other post-processing information. This post-processing is performed by the compounding processor 302, the scan converter 22 or other processors with access to the frames of data after storage in the memory 300.

Contrast within an image may be enhanced using histogram equalization. This produces an image making more uniform use of all available gray scale or amplitude levels (e.g., 0–255 levels). For a higher contrast image, some signals associated with more common amplitude levels are remapped to less common amplitude levels. As another example of contrast enhancement, the function applied by a look-up table to map contrast information with resolution information as described in U.S. Pat. No. 5,479,926, the disclosure of which is incorporated herein by reference, is selected by the user. The mapping function may be selected by the ultrasound system 304 as a function of the selected amount of compounding or a degree of correlation. The compounded frame of ultrasound data output by the compounding processor 302 is low-pass filtered. The original compounded frame of data output by the compounding processor 302 and the low-pass version are combined in the look-up table. The user or the ultrasound system 304 select between emphasizing the low-pass frame, emphasizing the original frame and emphasizing portions of both frames of data. In alternative embodiments, the compounded frame of data is treated as the low-pass filtered frame of data for look-up table combination with the original (non-compounded) frame of data.

As yet another example of post-processing, different color maps may be selected, such as a dark red to a bright orange map. Preferably, any color map selected is monotonic, providing a continuous color curve without sudden changes in color. Using a monotonic, color map avoids wrapping or combining two different colors to yield a third unrelated RGB or YUV value. For example, a red to orange to light orange color map is used and is less likely to produce wraparound effects, such as a blue and red color map. Likewise, preferably the gray scale is monotonic. Any spatial location based remapping, such as associated with edge enhancement or focal gain compensations, may also be adjusted.

Parameters associated with other compounding schemes may also be adjusted, such as parameters associated with the Energy Weighted Parameter Spatial/Temporal Filter disclosed in U.S. Pat. No. 5,609,155 or U.S. Pat. No. 5,899,864 (Ser. No. 08/827,863, filed Apr. 9, 1997), the disclosures of which are incorporated herein by reference.

Retrospective persistence may be used to aid in diagnosis. For example, the user scans the liver of a patient by translating the transducer array 14 ten centimeters in elevation. With a ten second sweep and a frame rate of 20 frames per second, a sequence of around 200 frames of ultrasound data are acquired and stored. Generally, each frame of ultrasound data is associated with a region spaced by one-half a millimeter in the elevation dimension. If imaging at 6 MHz, an optimal compounding distance may be associated with two millimeters in the elevation dimension. The user or the system 304 selects compounding of every four frames of ultrasound data to effectively provide two millimeter elevation spacing. Using equal weightings, the compounding processor 302 performs the following sequence of compounding.

$$(F1+F2+F3+F4)/4, (F2+F3+F4+F5)/4, (F3+F4+F5+F6)/4 \ldots (F197+F198+F199+F200)/4$$

where F1 is the first frame of data, F2 the second and so on.

If the resulting images are unsatisfactory or to be used for comparison purposes, the user selects a different amount of compounding, such as compounding every four frames using equal or different weighting co-efficients (e.g., 0.15, 0.35, 0.35, 0.15). The separately stored frames of ultrasound data are combined in a different way to provide different output compounded frames of ultrasound data and associated images. While persistence used in acquiring the frames of ultrasound data for storage in the memory 300 may not be altered for processing the stored frames of ultrasound data, the amount of compounding after storage may be adjusted.

For stress echo or other types of imaging, frames of data are obtained and synchronized with the heart cycle. Frames of data associated with particular portions of the heart cycle are persisted or compounded with frames of data associated with a different heartbeat but the same portion of the heartbeat. Therefore, the effects or smearing caused by movement of tissue are minimized.

III. USER INTERFACE

Various user interfaces may be used for providing adjustable retrospective persistence or other post-processing. One preferred embodiment is described below. Other user interfaces may be used.

A sequence of images associated with a sequence of frames of ultrasound data stored in the memory 300 may be viewed by the user, each separately or as a series to show movement. The user locates one or more frames of data of interest and may locate a region of interest within each of the frames of ultrasound data. The user may identify one particular image, may cause the system 304 to scroll forward or backwards to look at additional images in incremental steps or may cause the system 304 to play or reverse play the sequence to show motion. The user may cause the system 304 to mark the identified frames of data.

The user adjusts the amount of compounding, the brightness (i.e. mean pixel level), contrast (i.e. variance of pixel levels), or other post-processing for or during review of the stored frames of ultrasound data. For example, the amount of temporal persistence or compounding is continually adjusted as the sequence of images are played. Alternatively, the amount of compounding is applied to one frame of ultrasound data within the sequence. After identifying the one or more frames of data, the amount of compounding or other processing is selected, and the one or more frames of data are altered to correspond with the selected amount of compounding or processing. As the user scrolls through additional frames of ultrasound data and associated images, the selected amount of compounding is applied to the subsequent frames of ultrasound data for imaging.

In one embodiment, the user may select different amounts of persistence and other post-processing as a function of order within the sequence of frames of ultrasound data. One group of settings applies to a first subset of the sequence, and another one or more groups of settings would apply to a respective one or more different subsets of the sequence. For example, the user selects a range of frames of data and settings associated with that range. The user then selects a different range for different settings. In one preferred embodiment, the user marks the beginning and ending frames of data within each subset for convenient selection of each subset of frames of ultrasound data.

In one preferred embodiment, the user alternates between viewing an image associated with the same frame of ultrasound data with or without post-processing or compounding. Alternatively, both images are displayed at the same time in two adjacent areas of the display 38. Separate areas may be provided for displaying images associated with the same or different frames of ultrasound data, such as selecting key images within the sequence and displaying them simultaneously. The compounding settings may then be applied to all of the images or fewer than all of the images concurrently displayed.

The frames of data output by the compounding processor 302 may be stored in the memory 300 or another memory, such as a diskette or tape memory. Particular frames of ultrasound data output by the compounding processor 302 may be identified as of particular interest and saved in the memory 300 or another memory. Any non-selected frames of ultrasound data within a sequence may then be deleted from the memory 300. The memory 300 may be divided into original and processed memory. In an alternative embodiment, the amount of compounding and other post-processing settings are stored with the original frames of ultrasound data. The settings may be later applied to the original frames of ultrasound data to generate images associated with compounded frames of ultrasound data. For example, see section 4 below.

In one preferred embodiment, the user's ability to change the amount of compounding and other post-processing is modeless, allowing for continued processing or user input without regard to the state of user input. Preferably, the user independently adjusts any one or more of various post-processing attributes, such as the amount of compounding, brightness or contrast, for a given frame of data. The attribute is applied to subsequent frames of data or an entire sequence or clip of frames. For selecting an amount of compounding, the user is preferably provided with an adjustment to incrementally select the number of frames of ultrasound data to be compounded. Using a mouse, rollerball or holding down a key on a keyboard, the user increases or decreases the number of frames compounded. The compounding is changed immediately or after a delay in which further changes can occur, such as updating after each incremental change, updating only after a pause in changing to allow for a large discontinuous incremental change (e.g., a pause in movement of a mouse or rollerball), or only upon indication of completion or selection (e.g., releasing a depressed key).

In one embodiment, the left and right arrow keys are used to step through the frames of ultrasound data, and the up and down arrow keys are used to increase or decrease the number of frames of ultrasound data compounded together. In alternative embodiments, a button for stepping to preset persistence values is provided, such as previously stored filter settings. Preferably, the user may then further refine any of various post-processing settings.

Brightness and contrast are preferably adjusted in a similar way. The user selects a mode associated with brightness and contrast to allow changes in brightness and contrast without changing the amount of compounding. For example, turning on the brightness and contrast mode changes the function of the arrow keys in the preferred embodiment from selecting between frames of data and an amount of persistence to selecting brightness and contrast adjustments.

The typical brightness and contrast settings are represented by the function:

$$I'=\text{contrast}*I+\text{brightness},.$$

where I is an input pixel value and I' is a modified output pixel value. In one embodiment for providing user flexibility and to account for typical user settings, the brightness and contrast function is altered to be:

$$I'=\text{contrast}*(I+N)+\text{brightness}-N,$$

where N is a selectable value, such as 0–63 assuming a range of pixel levels from 0–255 (i.e., approximately 25% of full range).

In one embodiment, as the amount of compounding is adjusted, other settings are automatically updated, such as updating the brightness and contrast or other post-processing as a function of the amount of compounding.

IV. DATA COMPRESSION

In order to save memory space as well as processing time, the frames of ultrasound data may be transformed into compressed frames of ultrasound data prior to compounding. For example, the ultrasound system 304 transforms the frames of ultrasound data prior to transfer to a remote memory, such as the memory 300. Any of various transforms may be used for compression. For example, JPEG compression divides the frames of data into 8×8 blocks of data, performs a two-dimensional discrete cosine transform on each of the blocks, quantizes the result, changes a DC value to a DC difference from previous blocks, and performs entropy encoding (e.g., Huffman encoding). Other algorithms may be used. Generally, these algorithm functions are essentially linear but may include functions which are non-linear. Furthermore, variable code lengths may be produced due to entropy based encoding.

The compressed frames of ultrasound data are compounded as discussed above by the compounding processor. For example, the user inputs an amount of compounding or temporal persistence for use with a finite impulse response compounding filter, or correlation between compressed frames of ultrasound data is performed to determine an amount of compounding. The compounding is performed for non-real time analysis, such as providing for a 200 millisecond or more delay between storage and compounding of the compressed frames of ultrasound data.

In one preferred embodiment, the entropy coding process or another process of the compression algorithm is reversed by the compounding or another processor. Compression includes transform and quantization steps. Transforms include pure and modified transforms. A 'pure transform' is a transform which allows for near perfect inversion without additional processing. For example, Fast Fourier transforms and discrete cosine transforms are invertible. Data can be transformed back and forth. In JPEG, the DCT transform creates a 'pure transform' which is invertible back to original data. However, entropy encoding creates a 'modified transform'. Once the entropy encoding is performed, the inverse transform may not be performed without first undoing the 'modifying' step. The quantizing step of JPEG compression is a non-linear step and is non-invertible. However, it is designed to be approximately linear and hence invertible.

Color quantities in the image are preferably accounted for when combining JPEG data. JPEG separates the image into luminance (brightness) and chrominance (color density). Compounding the chrominance value may produce an undesirable result (e.g., red and blue Color Doppler signals are averaged to form an unrealistic color). Therefore, combination may be performed on the luminance quantities but not necessarily on the chrominance values. In this case the chrominance value for the most recent frames are associated with the compounded luminance frame. After combination, the compressed frames of ultrasound data are decompressed, such as performing the compression algorithm in the reverse order. After decompressing the frames of ultrasound data, an image or images are generated as discussed above.

Section 4—Image Re-Generation

Image re-generation provides for ultrasound image processing of ultrasound data to generate an image the same or similar to an image previously generated. Instead of transmitting or storing ultrasound data after applying various ultrasound image processes, ultrasound data existing before application of some or all the ultrasound image processes is transmitted or stored. Providing image re-generation may allow for maximum versatility for later imaging, such as at a remote workstation. For example, the same image is re-generated using the same ultrasound image processing previously used to generate the image. If the image is undesirable, other ultrasound image processes may be performed. Various examples of such versatility are disclosed in U.S. application Ser. No. 09/328,312, a Medical Diagnostic Ultrasound System and Method for Post-Processing filed herewith. As another example, different amounts of compounding, including persistence, may be applied as discussed in the various embodiments above.

I. ULTRASOUND SYSTEM

Referring now to FIG. 16, one preferred embodiment of a medical diagnostic ultrasound system for acquiring and ultrasound image processing ultrasound data for eventual re-generation of an image is shown generally at 410. Components labeled with different numbers in FIG. 16 and FIG. 1, 10 or 15 may comprise different components, different schematic representations of the same components or the same components. Preferably, the systems of two or more of these embodiments are provided on one ultrasound system, such as the systems corresponding to FIGS. 15 and 16. The system 410 may comprise ultrasound systems manufactured by Acuson Corporation under the trade names 128 XP, ASPEN, and SEQUOIA or systems manufactured by other ultrasound system manufacturers.

The system 410 includes a transmit beamformer 16 connected through a multiplexer 414 to a transducer 412. Echoes responsive to transmitted beams are received by the transducer 412 and passed through the multiplexer 414 to a receive path. The receive path includes a gain block 418, a receive beamformer 420, a focal gain compensation processor 422, a log compression device 424, a persistence processor 426, a memory 428, a filter 430, a post-processing look-up table 432, a scan converter, and a depth gain compensation processor 434. The system 410 also includes a display connected with the receive path and a central control computer 438 connected to various components of the receive path. Fewer or additional devices for ultrasound image processing may be provided. These devices may also be placed in a different order along the receive path. For example, the memory 428, is placed at any point along the receive path between the receive beamformer 420 and the display 436. The system 410 may comprise analog components, digital components or combinations thereof.

The central control computer 438 comprises one or more processors for controlling the acquisition of ultrasound data and subsequent ultrasound image processing. The central control computer 438 may be independent of, part of or partly a part of the devices for ultrasound image processing.

As used herein, ultrasound data broadly encompasses data at any one of various points or stages of processing within an ultrasound system, including electrical signals generated by a transducer in response to echoes, beamformed samples representing a line within the target, coherent or incoherent data, scan-converted data, or data prior to or after any of the various ultrasound image processing steps described herein.

Ultrasound data is subjected to various ultrasound image processes. An image responsive to the ultrasound image processing is generated. A parameter for the ultrasound image processing performed after storage or transmittal of a frame of ultrasound data is also stored or transmitted. The image is then re-generated in response to the transmitted or stored frame of ultrasound data and the parameter.

The gain block 418 comprises one type of ultrasound image processing. The gain block 418 comprises an amplifier, processor, multiplier or other hardware device for amplifying the ultrasound data provided from the transducer array 412. The gain provided by the gain block 418 is adjustable and controlled by the central control computer 438. The gain is adjusted as a function of user input or dynamically as a function of the signal-to-noise ratio. The amount of gain or another parameter used to determine the amount of gain comprises an ultrasound image processing parameter.

The amplified data output by the receive gain device 418 is provided to the receive beamformer 420. The receive beamformer 420 comprises a summer and optionally one or more filters. The receive beamformer 420 receives ultrasound data corresponding to a plurality of channels and sums the data. The summed ultrasound data represents the structure or fluid along a scan line within the target or patient. The receive beamformer 420, under the control of central control computer 438, is used to acquire a frame of ultrasound data associated with the type of imaging desired. For example, a frame of ultrasound data includes data representing a single point or region within the target for spectral Doppler imaging, a single scan line within the target for M-mode imaging, and a plurality of scan lines for two- or three-dimensional B-mode or motion imaging. Each frame of ultrasound data corresponds to substantially one time. A plurality of frames of ultrasound data acquired over time represent a sequence of frames of ultrasound data. The number of frames of ultrasound data acquired over a particular amount of time or within the sequence determines a frame rate.

The focal gain compensation look-up table 422 comprises a RAM or ROM memory device for ultrasound image processing. In alternative embodiments, a processor, multiplier or amplifier is used. Focal gain compensation look-up table 422 applies gain to ultrasound data as a function of a spatial location or proximity to the transmit beam focal point along each scan line. Focal gain compensation ultrasound image processing compensates for the increased energy associated with the focal point as compared to away from the focal point. Ultrasound data is generated with similar amplitudes regardless of the focal point. Focal gain compensation is performed as a function of a focal gain compensation parameter, such as one or more selectable look-up tables of output values given a particular input value for each spatial location along an ultrasound line. Other focal gain compensation parameters may be used, such as magnitude data provided by the central control computer 38 for varying the amplitude as a function of depth. Focal gain compensation may also include gain added to compensate for depth and frequency dependent attenuation. The focal gain compensation parameters are automatically applied based on pre-calculated data or data generated in real time under the control of the central control computer 438.

The ultrasound data is also provided to the log compression device 424 for further ultrasound image processing. The log compression device 424 comprises a digital signal processor, a processor, a look-up table memory or other device for log compressing the dynamic range of the ultrasound data. The acquired ultrasound data has a high dynamic range and the dynamic range is reduced by the log compression device 424. Log compression is performed in response to a dynamic range parameter. The dynamic range parameter comprises a desired range, such as 50–80 dB or another parameter for controlling log compression, such as data representing a user selection. Preferably, the log compression device 424 outputs ultrasound data rounded to and represented by eight bits of data per sample. A different number of bits or analog information may be used for representing the ultrasound data.

The ultrasound data is provided to the persistence processor 426 for further ultrasound image processing. The persistence processor 426 comprises a digital signal processor, a processor, or a filter for filtering through a sequence of ultrasound data (i.e. temporal filtering). In one preferred embodiment, the persistence processor 426 comprises an infinite impulse response (IIR) filter responsive to an IIR filtering parameter $\alpha$. $\alpha$ controls the weighting applied to the current and previous frames of ultrasound data within the sequence, as mathematically represented below:

$$I_{out}(i)=\alpha *I_{out}(i-1)+(1-\alpha)*I_{in}(i) \tag{1}$$

where for the $i^{th}$ frame I, $I_{in}$, is the input frame and $I_{out}$ is the output frame. In alternative embodiments, the persistence processor 426 performs finite impulse response (FIR) filtering, and the persistence filtering parameters comprise the type of FIR filter or the number of taps and various weights applied for FIR filtering. The weights applied or the $\alpha$ value used represent filter coefficients. The filter coefficients and associated filters may vary as a function of time or location within the frame of ultrasound data.

The persisted ultrasound data is stored in the memory 428. The memory 428 comprises a RAM, hard disk drive, a removable memory medium or other memory device for storing ultrasound data. The memory device 428 may perform CINE functions (e.g., short term image sequence loop storage for review either as a dynamic loop or sequence or as a single selected image). Preferably, the memory 428 receives IIR filter persisted ultrasound data since persistence with IIR filtering is reversible. When the IIR filtering includes only two inputs, the filtering operation is fully reversible. The stored ultrasound data may be compressed so that the amount of data is reduced while still allowing for other ultrasound image processing to work in a useful manner. In alternative embodiments, the memory 428 is provided along a different portion of the receive path, such as after the receive beamformer for storing raw beam ultrasound data (i.e. beam data not subjected to further ultrasound image processing).

In addition to persistence filtering, spatial filtering is provided by the filter 430 for further ultrasound image processing. The filter 430 comprises a processor, digital signal processor, or filter for implementing one or more of various filters. The various filters include IIR and/or FIR filtering. The filtering may be linear or nonlinear, and high pass or low pass. High-pass spatial filtering may be used to emphasize edges of structure within the target, and low-pass spatial filtering may be used to emphasize contrast within the target. In other embodiments, the filtering includes the combination of contrast ultrasound data with high resolution ultrasound data, such as taught in U.S. Pat. No. 5,479,926. Any of these various filtering functions are responsive to one or more filtering parameters. For example, the filter coefficients from an IIR or a FIR filter comprise filter parameters. The filter parameters may also include a number taps or spatial distribution of the kernel for spatial filtering. In the filter operation taught in U.S. Pat. No. 5,479,926 and possibly other filters, the filtering parameter comprises a look-up table or data for selecting or generating a look-up table. For any of these various filters, the filtering and associated filtering parameters may change as a function of depth or azimuthal location. The spatial filters and filtering parameters may also change as a function of time, such as different spatial filtering for different frames of ultrasound data.

The spatially filtered ultrasound data is transformed by the post-processing look-up table 432 as further ultrasound image processing. The post-processing look-up table 432 comprises a RAM or ROM memory device, a digital signal processor, a processor or other device for transforming the input ultrasound data into output ultrasound data to better emphasize data for imaging. The transform is typically represented by an S-shaped curve. This curve de-emphasizes low- and high-intensity data. Other curves may be used. In alternative embodiments, the curves vary as a function of depth and/or azimuthal position. For example, a two-dimensional mapping function is used. The post-processing curve parameter comprises the post-processing curve or data used for selecting or generating the post-processing curve or maps.

The transformed ultrasound data is provided to the scan converter 434. The scan converter comprises a device for reformatting polar coordinate ultrasound data into Cartesian coordinate ultrasound data.

The scan converter 434 may also comprise a RAM or ROM look-up table, processor, digital signal processor or other device for providing depth gain compensation. In one preferred embodiment, the gain applied at any particular depth or range of depths is a function of user input, such as input data provided by the central control computer 438 from user adjusted potentiometers or slides. This depth gain compensation comprises ultrasound image processing. In alternative embodiments, depth gain compensation is automatically controlled, such as disclosed in U.S. Pat. No. 5,579,768, where the depth gain compensation parameters comprise the variables used to determine the gain at different depths. The gain compensation parameter comprises an amplifier control value, a multiplier value (i.e. weight) or other parameter for adjusting the intensity or magnitude of ultrasound data.

Another ultrasound image processing operation is histogram equalization. The persistence processor 426 or another device discussed herein performs histogram equalization to create a more uniform histogram of gray scale values. Ultrasound data representing intensities is altered to enhance the contrast of resulting images using histogram equalization. The histogram equalization operation corresponds to a mapping function. This mapping function is stored for determining and applying an inverse function for reversal. The transformation used for histogram equalization may be changed on a frame-by-frame or subset of frames basis. The histogram equalization ultrasound image parameter comprises a curve representing the histogram process performed. Other parameters may be used.

While the devices for performing ultrasound image processing have been discussed above as individual or single devices, each may comprise more than one processor or other associated devices. One or more processors, digital signal processors, or look-up tables or other hardware may be used to implement two or more different ultrasound imaging processes. For example, one general processor may operate pursuant to software control for providing two or more of focal gain compensation, log compression, persistence filtering, spatial filtering, application of a processing curve, depth gain compensation, and other ultrasound image processing. Different types of ultrasound image processing, including known and yet to be developed processes, may be provided.

The ultrasound data from after the ultrasound image processes is output to the display 436 for generation of an image. The image is responsive to the various ultrasound image processing, such that adjustment of one or more of the ultrasound imaging processing parameters affects the image generated. Fewer than all of the ultrasound image processes discussed herein may be used to generate an image.

Ultrasound data used to generate the image on the display 436 and the associated processing parameters may be transmitted and/or stored for re-generation of the image of the display 436. For example, the scan converted ultrasound data from the scan converter 434 is provided to a compression processor 442. The compression processor 442 comprises a digital signal processor or other processor for compressing data. In one embodiment, JPEG or MPEG compression is used. The compression may be either lossy or a loss less, and may use frequency transformation, sampling, coding (e.g., Huffman coding or R.L.E. run length encoding), frame to frame motion estimation (e.g., to create persisted images), or other compression techniques. The compressed ultrasound data is provided to a network 446 or stored in a memory device 444. The network 446 may comprise the Internet, an intranet or a connection between any two processors. The storage device 444 may comprise a RAM memory, a hard disk drive, a floppy disk drive or other movable storage media. The storage device 444 may comprise the memory device 428. The storage device 444 may comprise a local or a remote memory.

Ultrasound data from other parts of the receive path may be input into the compression processor 442. Ultrasound data associated with one or more of various ultrasound image processes may be output from anywhere along the receive path to the compression processor 442. In alternative embodiments, the ultrasound data is not compressed prior to transmission to the network 446 or the storage device 444.

In one preferred embodiment, ultrasound data that is log compressed and temporally persisted without being spatially filtered, transformed pursuant to a post-processing curve, and altered for depth gain compensation is used for re-generating the image. The image is re-generated by applying the ultrasound image processing associated with one or more of the spatial filtering, post-processing curve transformation, and depth gain compensation that was applied to the ultrasound data for generation of the original image.

For this embodiment, the persisted ultrasound data is stored in the memory device 428 and provided on an output 440 for transmission to a remote processor. Alternatively, the central control computer 438 or another processor for re-generating the image from the ultrasound data from the memory device 428 or a removable storage medium.

The data transmitted or stored may comprise one or more of various types of data. For example 16-bit, 8-bit or other amounts of data for each sample may be used. The data may comprise in-phase and quadrature data (i.e., complex, baseband demodulated RF data), radio frequency (RF) data, or an intermediate frequency (IF) acoustic data, regardless of any log compression.

To account for adaptive or varying ultrasound image process parameters, the parameters stored or transferred with the frames of ultrasound data are transferred with each frame or as a header to a sequence of frames, depending on the frequency of change of any processing parameters. Preferably, one or more of the various ultrasound image processing parameters are stored with each frame of ultrasound data. The ultrasound image processing parameters associated with processes performed after storage of the ultrasound data are stored with or transmitted with the ultrasound data. These additional subsequent ultrasound image processing parameters may be used for re-generating an image substantially identical to the image that was previously generated on the display 436. In the embodiment discussed above where persistence processing has been performed without subsequent ultrasound image processing, the ultrasound image processing parameters associated with spatial filtering, application of a post-processing curve, and depth gain compensation used to generate a real-time image are stored or transmitted with the ultrasound data. Using this information, a same image may be re-generated from the ultrasound data off-line during a later review.

Ultrasound image processing parameters for each of the ultrasound imaging processes performed on the stored or transmitted ultrasound data may also be stored or transmitted with that ultrasound data.

Alternatives to transmitting or storing the ultrasound image processing parameters may be used. In one alternative, an index or other representation of the ultrasound image processing parameter that was performed on the ultrasound data after storage or transmission is used. For example, a numerical description of the image processing parameters may be used. Where look-up tables or other complex ultrasound image processing parameters are provided, an index method is preferably used. Based on the index value, a known or common look-up table entry (e.g., a look-up table existing or accessible at both a source and a destination) or other ultrasound image processing parameter may be obtained for re-generating the image by using the same ultrasound image processing.

In addition to the ultrasound image processing parameters, other information associated with the frames of ultrasound data is stored and/or transmitted. For example, the frame rate is stored. The actual time of acquisition or a time of acquisition relative to a physiological event or other signal, such as an ECG or injection of a contrast agent, is also stored or transmitted with the frame of ultrasound data. Patient information, including date of birth, social security number, date of acquisition and other information, such as provided for in the DICOM standard, is also provided. The ultrasound data and associated ultrasound image processing parameters and other stored information may be transmitted and/or stored pursuant to the DICOM standard with additional data fields provided as needed. Other formats may be used, such as TIFF or BMP. In alternative embodiments, a proprietary format is used.

The ultrasound data, either raw beam data or data having been ultrasound image processed for some, but not all, the processes used to generate an image is provided to a system for re-generation of the image. Re-generation is performed by a remote system or by the ultrasound system 410. If performed by the ultrasound system 410, the central control computer 438 or another processor obtains stored ultrasound data from the memory 428, the memory 444 or another memory for re-generating the image as discussed below. For re-generation by a remote processor, an ultrasound system or a workstation comprising a remote processor receives the transmitted data or acquires the data from a storage device and performs the re-generation of the image as discussed below.

In one embodiment, the remote system re-generates the image in real-time with the acquisition system, such as to allow monitoring at another location of the imaging session. Alternatively, the remote system is used after the imaging session has ended to re-generate the image.

Figure 17:
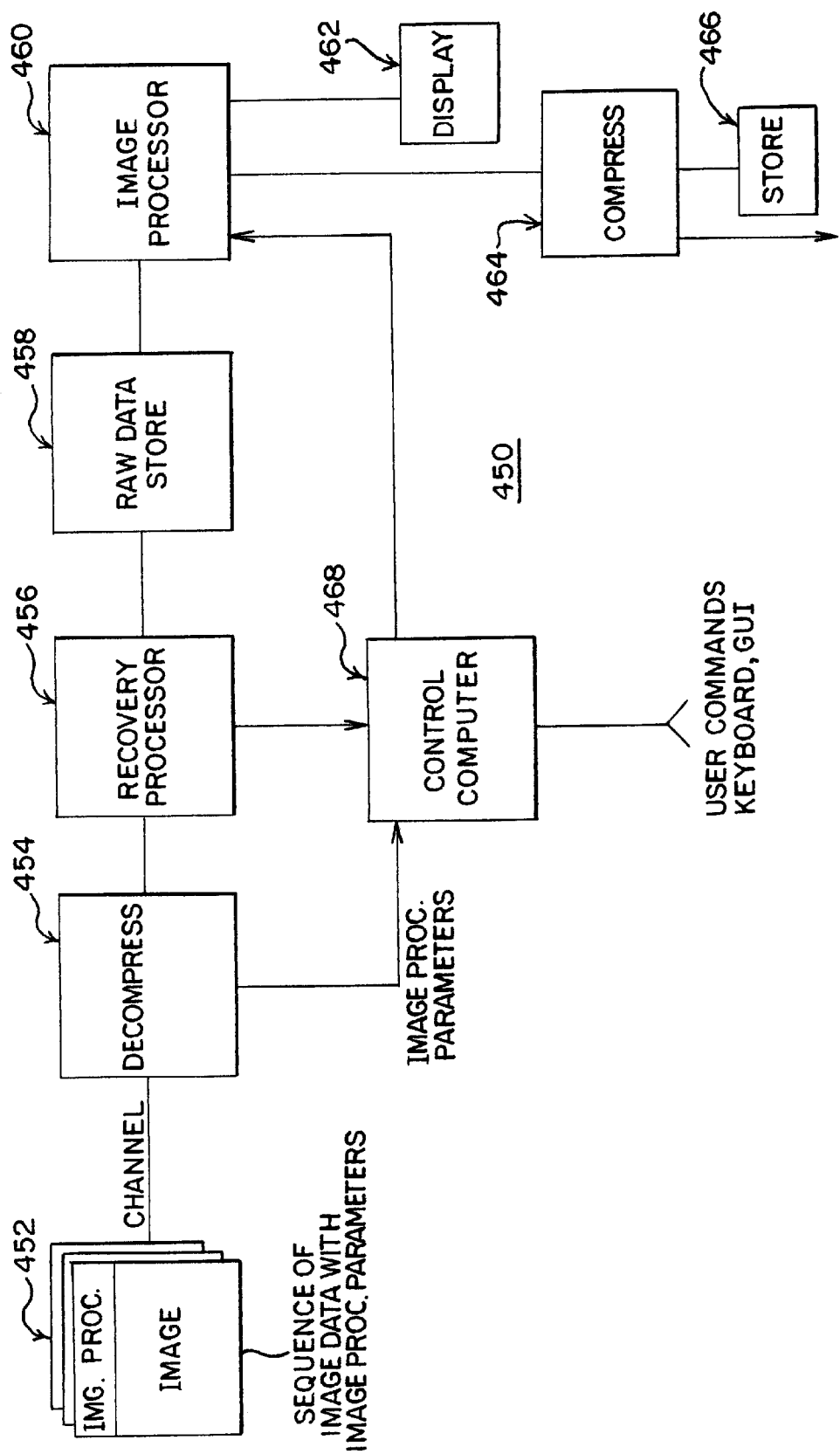
FIG. 17 is a block diagram of one embodiment of a remote system for re-generating an image.

Referring to FIG. 17, one embodiment of a medical diagnostic ultrasound system for reviewing ultrasound images by re-generating an ultrasound image is shown generally at 450. The system 450 comprises components of the ultrasound system 410 of FIG. 16 or components of a remote ultrasound system. For example, the system 450 comprises a picture archiving computer system or other processor, such as an AEGIS ultrasound system manufactured by Acuson Corporation. Other remote systems and processors may be used.

The system 450 includes an optional decompression processor 454, an optional recovery processor 456, a memory device 458, an image processor 460, a display 462, an optional compression processor 464, and an optional memory device 466. A control computer 468 controls the operation of these various components. A same device may be used for two or more of the various components of the system 450. For example, the decompression processor 454 and the compression processor 464 may comprise a single digital signal processor. As another example, the recovery processor 456, the image processor 460, and optionally the control computer 468 comprise a single one or a group of processors for performing each of the processes associated with these processors as discussed below.

The system 450 obtains a sequence of frames of ultrasound data as represented by the block 452. The sequence is obtained from a target, from a transmission of ultrasound data or from a storage or memory device. Devices operable to obtain the ultrasound data include memory devices, network devices (e.g., the Internet, an intranet, a port connected to a network) and other processors for receiving or acquiring data. The ultrasound data of the sequence has been previously used to generate an image in response to ultrasound image processing.

In one preferred embodiment, ultrasound data associated with motion detection (e.g., color Doppler processing) is sent separately from ultrasound data associated with B-mode detection. Processes associated with each type of ultrasound data may be re-performed independently of each other. Separate filter coefficients or ultrasound processing parameters may be provided for each of motion related and B-mode related ultrasound data. In alternate embodiments, the motion detected ultrasound data and B-mode data are combined, such as associated with a color Doppler overlay of a gray scale B-mode image. Preferably, the combined ultrasound data is separated prior to applying any of the ultrasound image processing for re-generation. One way of performing color separation or separation of this data is disclosed in U.S. application Ser. No. 09/196,986, filed Nov. 20, 1998, the disclosure of which is incorporated herein by reference. A color superimposing step can be used which mixes Doppler Color and B-mode speckle. Thereafter, the B-mode speckle is processed by referring to the Color lookup table and inferring the underlying B-mode value. If necessary, the B-mode values are rescaled if they were scaled during the color mapping process.

If the obtained ultrasound data is compressed, the decompression processor 54 decompresses the data. Preferably, the decompression processor 54 comprises a digital signal processor or other processor for decompressing data, such as JPEG or MPEG decompression processors. In alternative embodiments, the ultrasound data is not compressed or is to remain compressed, so the decompression processor 54 is not provided or is bypassed.

After any decompression, ultrasound image processing may reversed, at least in part, by the recovery processor 56. The recovery processor 56 comprises a general processor operating pursuant to software control, a digital signal processor, hardware devices, such as dividers, multipliers, adders and subtractors, or RAM or ROM look-up tables appropriate for the reversal of one or more ultrasound image processes. Ultrasound data from before application of one or more ultrasound image processes may be recovered, such as disclosed in U.S. application Ser. No. 09/328,312, filed herewith, and then used to re-generate a same or different image.

The frames of ultrasound data are used to re-generate an image on the display 462. In a preferred embodiment where some recovery of data through reversing ultrasound image processing is performed, the recovered frames of ultrasound data are stored prior to generation of an image on the display 462. For example, the recovered frames of ultrasound data are stored in the memory 458. The memory 458 comprises a RAM, a hard drive, a removable storage medium or other memory devices for storing ultrasound data.

The image processor 460 accesses the recovered frames of ultrasound data, such as from the memory 458, or otherwise obtains the stored or transmitted frames of ultrasound data. The image processor 460 comprises one or more digital signal processors, general processors operating pursuant to software control, or other hardware devices such as the devices discussed above with respect to one or more of each type of ultrasound image processing. The image processor 460 performs ultrasound image processing on the frames of ultrasound data to re-generate the previously displayed image.

The image processor 460 operates in response to instructions from the control computer 468. Based on user input, the frames of ultrasound data are processed to re-generate the image. The user selects re-generation of the previous image. The image processor 460 applies ultrasound image processing as a function of the ultrasound image processing parameters provided for the ultrasound data. Preferably, only the ultrasound image processes and associated parameters used to generate the original image subsequent to storage or transmission of the ultrasound data are used by the image processor 460.

Different amounts and types of ultrasound image processing may be applied to generate a different image based on the same ultrasound data. In order to provide the user with the maximum versatility, the image processor 460 is operable to obtain the frames of ultrasound data and apply ultrasound image processing in different ways or apply different ultrasound image processes for generating a different image. The user views an image different from the original image in an attempt to better identify diagnostic information.

In one embodiment, the sequence of ultrasound data represented by block 452 comprises ultrasound data subjected to some ultrasound image processing, but not other ultrasound image processing. For example, ultrasound data associated with log compression, focal gain compensation, and persistence processing is provided without having been subjected to spatial filtering, post-processing transformation and depth gain compensation. The image processor 460 applies one or more ultrasound image processes, such as spatial filtering and post-processing transformation, to re-generate the image.

In one embodiment, the user is offered a menu of various ultrasound image processing parameters, including the parameters for use to re-generate the previous image. Alternatively, the system 50 automatically selects the parameter or parameters for re-generation. The parameters may include one or more of the post-processing curve, depth gain control designated through a graphic user interface (e.g., analog potentiometers) or a system determined amount of depth gain compensation, a filter (e.g., spatial filtering, edge enhancing filters (e.g., high pass filters), smoothing filters (e.g., low pass filters), contrast enhancing filters (e.g., filters discussed in U.S. Pat. No. 5,479,926), linear or nonlinear filtering (e.g., thresholding), and/or median filtering), and histogram equalization for a contrast enhancement.

Where a sequence of images were provided, the parameters associated with the sequence or each frame are provided for re-generation of the plurality of images. Since the parameters may change as a function of time or spatial location, the parameters stored or transmitted with the ultrasound data also preferably reflect these changes.

While the invention has been described above by reference to various embodiments, it will be understood that many changes and modifications can be made without departing from the scope of the invention. For example, different combinations, relationships and processors may be used. The processors 20, 24, 28 and 32 may comprise one processor. Different groupings or sets of frames of data may be used. The reconstruction computer may include the compounding filter whether compounding prior to or after 3D reconstruction. The compounding may comprise a FIR filter or a summer. Any of various imaging modes or combinations of modes may also be used. Any of the various systems described above may be used to implement any of the embodiments described above.

Lastly, the following patent applications, which are assigned to the assignee of the present patent application, are hereby incorporated by reference: "Method and System for Simultaneously Displaying Diagnostic Medical Ultrasound Image Clips," Ser. No. 09/200,170, filed Nov. 25, 1998 and "Medical Diagnostic Ultrasound System and Method for Transform Ultrasound Processing," Ser. No. 09/200,021.

It is therefore intended that the foregoing detailed description be understood as an illustration of the presently preferred embodiments of the invention, and not as a definition of the invention. It is only the following claims, including all equivalents, which are intended to define the scope of this invention.

APPENDIX A

Filter at Plane Y = −2

X →

$$\begin{bmatrix} 0.0 & 0.0 & 0.0 & 0.0 & 0.0 \\ 0.0 & 0.0 & 0.0 & 0.0 & 0.0 \\ 0.0 & 0.0 & 0.2 & 0.0 & 0.0 \\ 0.0 & 0.0 & 0.0 & 0.0 & 0.0 \\ 0.0 & 0.0 & 0.0 & 0.0 & 0.0 \end{bmatrix} \begin{matrix} Z \\ \downarrow \end{matrix}$$

Filter at Plane Y = −1

$$\begin{bmatrix} 0.0 & 0.0 & 0.0 & 0.0 & 0.0 \\ 0.0 & 0.0 & 0.0 & 0.0 & 0.0 \\ 0.0 & 0.0 & 0.4 & 0.0 & 0.0 \\ 0.0 & 0.0 & 0.0 & 0.0 & 0.0 \\ 0.0 & 0.0 & 0.0 & 0.0 & 0.0 \end{bmatrix}$$

Filter at Plane Y = 0

$$\begin{bmatrix} 0.0 & 0.0 & 0.0 & 0.0 & 0.0 \\ 0.0 & 0.0 & 0.0 & 0.0 & 0.0 \\ 0.0 & 0.0 & 1.0 & 0.0 & 0.0 \\ 0.0 & 0.0 & 0.0 & 0.0 & 0.0 \\ 0.0 & 0.0 & 0.0 & 0.0 & 0.0 \end{bmatrix}$$

Filter at Plane Y = +1

$$\begin{bmatrix} 0.0 & 0.0 & 0.0 & 0.0 & 0.0 \\ 0.0 & 0.0 & 0.0 & 0.0 & 0.0 \\ 0.0 & 0.0 & 0.4 & 0.0 & 0.0 \\ 0.0 & 0.0 & 0.0 & 0.0 & 0.0 \\ 0.0 & 0.0 & 0.0 & 0.0 & 0.0 \end{bmatrix}$$

-continued

Filter at Plane Y = +2

$$\begin{bmatrix} 0.0 & 0.0 & 0.0 & 0.0 & 0.0 \\ 0.0 & 0.0 & 0.0 & 0.0 & 0.0 \\ 0.0 & 0.0 & 0.2 & 0.0 & 0.0 \\ 0.0 & 0.0 & 0.0 & 0.0 & 0.0 \\ 0.0 & 0.0 & 0.0 & 0.0 & 0.0 \end{bmatrix}$$

The filter performs no filtering in the X, Z plane. It filters (low pass) contributions from neighboring elements in only the Y direction. The filter may be implemented as a 1-D low pass filter in the Y-direction [0.2, 0.4, 1.0, 0.4, 0.2]=(a 1×5×1 anisotropic filter).

What is claimed is:

1. A method for generating a compounded image with an ultrasound system, the method comprising the steps of:
   (a) acquiring a sequence of at least three frames of ultrasound data;
   (b) storing each of the at least three frames of ultrasound data separately;
   (c) inputting compounding information from a user;
   (d) compounding at least two of the at least three frames of ultrasound data in response to the compounding information, an finite impulse response and after step (b); and
   (e) displaying a compounded image responsive to step (d).

2. The method of claim 1 wherein step (a) comprises acquiring the ultrasound data with a one-dimensional transducer array.

3. The method of claim 1 wherein step (d) comprises compounding with a finite impulse response filter.

4. The method of claim 3 wherein step (d) comprises compounding the at least three frames of ultrasound data.

5. The method of claim 4 wherein step (d) comprises:
   (d1) multiplying the at least three frames of ultrasound data by at least three respective weights with a finite impulse response filter; and
   (d2) summing the weighted at least three frames of ultrasound data with the finite impulse response filter.

6. The method of claim 3 wherein step (e) comprises displaying a series of compound images, wherein each compound image in the series is responsive to a different set of the separately stored sequence of at least three frames of ultrasound data.

7. The method of claim 1 wherein step (c) comprises inputting a temporal persistence value.

8. The method of claim 7 wherein step (c) comprises determining a filter size and weighting coefficients in response to the temporal persistence value.

9. The method of claim 7 further comprising the steps:
   (f) inputting additional compounding information after step (e);
   (g) compounding the at least two of the at least three frames of ultrasound data in response to the additional compounding information; and
   (h) displaying an additional compounded image responsive to step (g).

10. The method of claim 1 where steps (b), (d) and (e) are performed by a processor remote from the ultrasound system.

11. The method of claim 1 further comprising:
   (f) transforming the at least three frames of ultrasound data responsive to step (f); and
   wherein step (d) comprises compounding transformed compressed ultrasound data responsive to step (f).

12. The method of claim 11 wherein step (f) comprises compressing the at least three frames of ultrasound data; and
   wherein step (d) comprises compounding compressed ultrasound data.

13. The method of claim 11 further comprises (g) accounting for non-linear processes in step (f) prior to step (d).

14. The method of claim 1 further comprising (f) of aligning the at least two of the at least three frames of ultrasound data in a spatial parameter selected from the group consisting of: range, azimuth, rotation and combinations thereof prior to steps (d).

15. The method of claim 14 further comprising determining alignment information for step (f) as a function of a region of interest.

16. The method of claim 1 wherein step (a) comprises acquiring the sequence, wherein each of the at least three frames of ultrasound image date is associated with at least one point in an elevation position different than an equivalent point in another of the at least three frames of ultrasound data.

17. The method of claim 1 wherein:
   step (a) comprises acquiring the sequence wherein each of the at least three frames of ultrasound data represent a substantially same region; and
   step (d) comprises temporally persisting the at least two of the at least three frames of ultrasound data.

18. The method of claim 1 wherein at least 200 milliseconds passes between steps (b) and (d).

19. The method of claim 1 wherein step (a) comprises acquiring the sequence wherein each of the at least three frames of ultrasound data comprises persisted frames of ultrasound data.

20. The method of claim 1 wherein steps (c), (d), and (e) are performed during a non-real time review.

21. The method of claim 1 wherein step (d) comprises compounding in response to a non-linear function.

22. The method of claim 1:
   wherein step (c) comprises inputting user selected alteration information;
   further comprising (f) of altering the compounded ultrasound data responsive to step (d); and
   wherein step (e) is responsive to step (f).

23. An ultrasound system for generating a compounded image, the system comprising:
   a beamformer for acquiring a sequence of at least three frames of ultrasound data;
   a memory for storing each of the at least three frames of ultrasound data separately;
   a user interface for inputting compounding information;
   a finite impulse response compounding processor for compounding at least two of the at least three frames of ultrasound data in response to the compounding information and after storage of each of the at least three frames of ultrasound data; and
   a display for displaying a compounded image responsive to step (d).

24. The system of claim 23 wherein the compounding processor comprises a finite impulse response filter.

25. The system of claim 23 wherein the display is operable to display a series of compound images, wherein each compound image in the series is responsive to a different set of the separately stored sequence of at least three frames of ultrasound data.

26. The system of claim 23 wherein the compounding information comprises a number of frames to compound.

27. The system of claim 23 wherein the user interface is operable to receive additional compounding information after the display of the compounded image;
the compounding processor is operable to compound the at least two of the at least three frames of ultrasound data in response to the additional compounding information; and
the display is operable to display an additional compounded image responsive to step (g).

28. The system of claim 23 where the memory and the compounding processor comprise a workstation remote from the ultrasound system.

29. The system of claim 23 wherein at least 200 milliseconds passes between storage and compounding.

30. A method for generating a compounded image with an ultrasound system, the method comprising the steps of:
(a) acquiring the sequence of at least two frames of ultrasound data;
(b) storing a sequence of at least two frames of ultrasound data representing a substantially same two-dimensional region;
(c) compounding the at least two frames of ultrasound data with a finite impulse response filter; and
(d) displaying a compounded image responsive to step (b).
wherein at least 200 milliseconds passes after step (b) and before performing step (d).

31. The method of claim 30 further comprising step (e) of acquiring the sequence of at least two frames of ultrasound data with a one-dimensional transducer array.

32. The method of claim 30 wherein step (c) comprises compounding at least three frames of ultrasound data.

33. The method of claim 30 wherein step (c) comprises:
(c1) multiplying the at least two frames of ultrasound data by at least two respective weights; and
(c2) summing the weighted at least two frames of ultrasound data.

34. The method of claim 30 wherein:
step (b) comprises storing the at least two frames of ultrasound data separately; and
step (d) comprises displaying a series of compound images, wherein each compound image in the series is responsive to a different set of the separately stored sequence of at least two frames of ultrasound data, where each different set is independent of at least one of the separately stored sequence of at least two frames of ultrasound data of at least one of the other sets.

35. The method of claim 30 further comprising:
(e) inputting persistence information from a user.

36. The method of claim 35 wherein step (e) comprises determining a filter size and weighting coefficients in response to the persistence information.

37. The method of claim 36 further comprising the steps:
(f) inputting additional persistence information after step (d);
(g) compounding the at least two frames of ultrasound data in response to the additional persistence information; and
(h) displaying an additional compounded image responsive to step (g).

38. The method of claim 30 where steps (b), (c) and (d) are performed by a processor, remote from the ultrasound system.

39. The method of claim 30 further comprising:
(e) transforming the at least two frames of ultrasound data; and
wherein step (c) comprises compounding transformed ultrasound data.

40. The method of claim 39 wherein step (e) comprises compressing the at lest two frames of ultrasound data.

41. The method of claim 30 further comprising (e) of aligning the at least two frames of ultrasound data in a spatial parameter selected from the group consisting of: range, azimuth, rotation and combinations thereof prior to step (c).

42. The method of claim 41 further comprising determining alignment information for step (e) as a function of a region of interest.

43. The method of claim 41 wherein step (a) comprises acquiring the sequence, wherein each of the at least two frames of ultrasound image date is associated with at least one point in an elevation position different than an equivalent point in another of the at least two frames of ultrasound data.

44. The method of claim 30 wherein step (a) comprises acquiring the sequence wherein each of the at least two frames of ultrasound data comprises persisted frames of ultrasound data.

45. The method of claim 30 wherein steps (c) and (d) are performed during a non-real time review.

46. The method of claim 45 wherein step (b) comprises storing the sequence in a CINE memory.

47. The method of claim 30 wherein step (c) comprises compounding in response to a non-linear function.

48. The method of claim 30 further comprising:
(e) of inputting user selected alteration information selected from the group consisting of: histogram equalization, contrast and resolution mapping function, and combinations thereof; and
(f) of altering the compounded ultrasound data resulting from step (c) in response to the user selected alteration information; and
wherein step (d) is responsive to step (f).

49. The method of claim 30 further comprising:
(e) determining a degree of correlation between the at least two frames of ultrasound data; and
wherein step (c) is responsive to the correlation.

50. An ultrasound system for generating a compounded image, the system comprising:
a beamformer for acquiring the sequence of at least two frames of ultrasound data;
a memory for storing a sequence of at least two frames of ultrasound data representing a substantially same two-dimensional region;
a finite impulse response filter for compounding the at least two frames of ultrasound data; and
a display for displaying a compounded image responsive to an output of the finite impulse response filter;
wherein at least 200 milliseconds passes after storage of the sequence and compounding.

51. The system of claim 50 wherein:
the memory is operable to store the at least two frames of ultrasound data separately; and
wherein the display is operable to display a series of compound images, wherein each compound image in the series is responsive to a different set of the separately stored sequence of at least two frames of ultrasound data, where each different set is independent of at least one of the separately stored sequence of at least two frames of ultrasound data of at least one of the other sets.

52. The system of claim 50 further comprising a user interface operable to receive compounding input information selected from the group consisting of: a filter size and weighting coefficients.

53. The system of claim 52 wherein:

the user interface is operable to receive additional compounding input information after the display of the compounded image;

the filter is operable to compounding the at least two frames of ultrasound data in response to the additional compounding input information; and the display is operable to display an additional compounded image responsive to the additional compounding input information.

54. A method for generating a compounded image with an ultrasound system, the method comprising the steps of:

(a) acquiring first and second two-dimensional frames of ultrasound data, each two-dimensional frame of ultrasound data associated with a different elevation position than each other two-dimensional frame of data;

(b) determining a degree of correlation between the first and second frames of ultrasound data;

(c) compounding the first and second two-dimensional frames of ultrasound data less if the degree of correlation is low and more if the degree of correlation is high;

(d) displaying a compounded image responsive to step (c).

55. The method of claim 54 further comprising:

(e) transforming the first and second frames of ultrasound data; and wherein step (c) comprises compounding the transformed ultrasound data.

56. The method of claim 55 wherein step (e) comprises compressing the first and second frames of ultrasound data.

57. The method of claim 54 further comprising (e) of aligning the first and second frames of ultrasound data in a spatial parameter selected from the group consisting of: range, azimuth, rotation and combinations thereof prior to step (c).

58. The method of claim 57 further comprising determining an alignment correlation;

wherein step (e) is a function of the alignment correlation.

59. The method of claim 58 further comprising determining the alignment correlation as a function of a region of interest.

60. The method of claim 54 wherein step (c) comprises compounding with a finite impulse response filter.

61. The method of claim 54 further comprising:

(e) storing the first and second two-dimensional frames of ultrasound data;

(f) inputting user persistence information;

wherein step (c) is responsive to the user persistence information and occurs at least 200 milliseconds after step (a).

62. The method of claim 54 wherein step (b) comprises calculating a minimum sum of absolute differences.

63. The method of claim 54 wherein step (c) comprises:

(c1) compounding more as selected from the group consisting of: using more evenly distributed weights, including additional two-dimensional frames of ultrasound data, and combinations thereof; and (c2) compounding less as selected from the group consisting of: weighting the second two-dimensional frame of ultrasound data more than other frames of two-dimensional ultrasound data, including fewer two-dimensional frames of ultrasound data, and combinations thereof.

64. The method of claim 54 further comprising:

(e) repeating steps (a), (b), (c), and (d) for at least three sets of frames of ultrasound data; and wherein step (c) comprises interpolating the degree of correlation for one of the at least three sets from the degree of correlation from another one of the at least three sets.

65. The method of claim 54 further comprising:

(e) inputting a user selected correlation coefficient threshold.

66. The method of claim 54 wherein step (b) comprises determining the degree of correlation from data selected from the group consisting of: data associated with a near field image region and data prior to focal gain compensation.

67. An ultrasound system for generating a compounded image, the system comprising:

first and second two-dimensional frames of ultrasound data, each two-dimensional frame of ultrasound data associated with a different elevation position than each other two-dimensional frame of data;

a compounding processor for determining a degree of correlation between the first and second frames of ultrasound data and for compounding the first and second two-dimensional frames of ultrasound data less if the degree of correlation is low and more if the degree of correlation is high; and a display for displaying a compounded image responsive to the output of the compounding processor.

68. The system of claim 67 wherein the compounding processor is operable to compound compressed ultrasound data.

69. The system of claim 67 wherein step the compounding processor comprises a finite impulse response filter.

70. The system of claim 67 further comprising:

a memory operable to store the first and second two-dimensional frames of ultrasound data; and a user interface operable to receive user persistence information;

wherein the compound processor is responsive to the user persistence information and compounds at least 200 milliseconds after storage in the memory.

71. A method for generating a compounded image with an ultrasound system, the method comprising the steps of:

(a) transforming first and second frames of ultrasound data;

(b) compounding the first and second frames of ultrasound data;

(c) decompressing a compounded frame of ultrasound data responsive to step (b); and (d) displaying an image responsive to the compounded frame of ultrasound data.

72. The method of claim 71 wherein step (a) comprises transforming pursuant to at least one step of JPEG compression steps and step (c) comprises decompressing pursuant to at least one step of JPEG decompression steps.

73. The method of claim 71 further comprising:

(e) transforming the compressed first and second frames of ultrasound data as a function of a pure transform operation in step (a) prior to step (b).

74. The method of claim 71 further comprising:

(e) inputting persistence information from a user;

wherein step (b) is responsive to the temporal persistence information.

75. The method of claim 71 further comprising:

(e) determining a filter size and at least one weighting coefficient as a function of user provided compounding information;

wherein step (b) is responsive to the filter size and the at least one weighting coefficient.

76. The method of claim 71 wherein step (b) comprises compounding with a finite impulse response filter.

77. The method of claim 71 further comprising:

(e) determining a degree of correlation relating the first and second frames of ultrasound image; and wherein step (b) is responsive to the degree of correlation.

78. The method of claim 71 further comprising:

(e) acquiring the first and second frames of ultrasound data;

(f) storing the first and second frames of ultrasound data separately;

wherein at least 200 milliseconds passes between steps (f) and (d).

79. The method of claim 77 wherein steps (b), (c), and (d) are performed during a non-real time review.

80. An ultrasound system for generating a compounded image, the system comprising:

first and second frames of transformed ultrasound data;

a compounding processor for compounding the first and second frames of ultrasound data and for decompressing a compounded frame of ultrasound data; and a display for displaying an image responsive to the compounded frame of ultrasound data.

81. The system of claim 80 wherein the compounding processor is operable to perform JPEG decompression.

82. The system of claim 80 further comprising:

a user interface for receiving input persistence information;

wherein the compounded frame of ultrasound data is responsive to the persistence information.

83. The system of claim 80 further comprising:

a beamformer for acquiring the first and second frames of ultrasound data; and a memory for storing the first and second frames of ultrasound data separately;

wherein at least 200 milliseconds passes between storing and compounding the first and second frames of ultrasound data.

84. The method of claim 1 further comprising:

(f) alternatively displaying another image responsive to one of the at least three frames of ultrasound data and different compounding after step (e).

85. The method of claim 84 wherein steps (e) and (f) are performed during the display of the sequence.

86. The method of claim 84 further comprising:

(g) applying different processing selected from the group consisting of: brightness, contrast, and combinations thereof to the compounded image than to the other image.

87. The method of claim 1 wherein step (c) comprises selecting preset persistence values.

88. The method of claim 87 further comprising:

(f) automatically adjusting one or both of brightness and contrast in response to the input of the compounding information.

89. The method of claim 1 wherein step (c) comprises selecting incremental values.

90. The method of claim 1 further comprising:

(f) adjusting one or both of brightness and contrast of the compounded image in response to a user selectable value.

\* \* \* \* \*